US009585993B2

(12) United States Patent
Childers et al.

(10) Patent No.: US 9,585,993 B2
(45) Date of Patent: Mar. 7, 2017

(54) METHOD OF PERFORMING PERITONEAL DIALYSIS USING PNEUMATIC VALVES

(71) Applicants: Baxter International Inc., Deerfield, IL (US); Baxter Healthcare S.A., Glattpark (Opfikon) (CH)

(72) Inventors: Robert Childers, Trinity, FL (US); Scott Keeling, Holiday, FL (US); Li Pan, Arcadia, CA (US)

(73) Assignees: Baxter International Inc., Deerfield, IL (US); Baxter Healthcare SA, Glattpark (Opfikon) (CH)

( * ) Notice: Subject to any disclaimer, the term of this patent is extended or adjusted under 35 U.S.C. 154(b) by 83 days.

(21) Appl. No.: 14/079,321

(22) Filed: Nov. 13, 2013

(65) Prior Publication Data
US 2014/0074018 A1    Mar. 13, 2014

Related U.S. Application Data

(63) Continuation of application No. 13/550,243, filed on Jul. 16, 2012, now Pat. No. 8,597,231, which is a
(Continued)

(51) Int. Cl.
| | | |
|---|---|---|
| *A61M 1/00* | (2006.01) | |
| *A61M 1/28* | (2006.01) | |
| *A61M 1/16* | (2006.01) | |

(52) U.S. Cl.
CPC ............ *A61M 1/28* (2013.01); *A61M 1/1643* (2014.02); *A61M 1/281* (2014.02); *A61M 1/282* (2014.02);
(Continued)

(58) Field of Classification Search
CPC ...... A61M 1/28; A61M 1/2811; A61M 1/282; A61M 1/288; A61M 1/1643; A61M 1/0023
See application file for complete search history.

(56) References Cited

U.S. PATENT DOCUMENTS

| | | | | |
|---|---|---|---|---|
| 3,730,183 A | * | 5/1973 | Goldsmith | ............... A61M 1/28 604/29 |
| 3,783,866 A | | 1/1974 | Tirkkonen | |

(Continued)

FOREIGN PATENT DOCUMENTS

| | | |
|---|---|---|
| FR | 2371931 | 7/1978 |
| FR | 2397197 | 2/1979 |

(Continued)

OTHER PUBLICATIONS

Article entitled "How to Prescribe an Optimal APD Regime" from Amici and Thomaseth, Contrib Nephrol 1999, pp. 12-13.
(Continued)

*Primary Examiner* — Andrew Gilbert
(74) *Attorney, Agent, or Firm* — K&L Gates LLP

(57) ABSTRACT

A method of performing peritoneal dialysis includes: (i) locating a supply of fresh dialysis fluid above a patient's peritoneal cavity; (ii) locating a drain or a drain container below the patient's peritoneal cavity; (iii) connecting a supply line to the supply of fresh dialysis fluid and the patient's peritoneal cavity; (iv) connecting a drain line to the patient's peritoneal cavity and the drain or drain container; (v) pneumatically opening a supply line valve during a fill cycle; (vi) gravity filling the patient's peritoneal cavity with the supply line valve open during the fill cycle; (vii) pneumatically opening a drain line valve during a drain cycle; and (viii) draining the patient's peritoneal cavity with the drain line valve open during the drain cycle.

21 Claims, 13 Drawing Sheets

Related U.S. Application Data continuation of application No. 11/420,608, filed on May 26, 2006, now Pat. No. 8,226,595.

(52) U.S. Cl.
CPC ........... *A61M 1/288* (2014.02); *A61M 1/0023* (2013.01); *A61M 2205/12* (2013.01)

(56) References Cited

U.S. PATENT DOCUMENTS

| | | | |
|---|---|---|---|
| 4,132,644 A | 1/1979 | Kolberg | |
| 4,178,240 A | 12/1979 | Pinkerton | |
| 4,190,047 A | 2/1980 | Jacobsen et al. | |
| 4,204,957 A | 5/1980 | Weickhardt | |
| 4,240,408 A | 12/1980 | Schael | |
| 4,301,879 A | 11/1981 | Dubow | |
| 4,318,447 A | 3/1982 | Northcutt | |
| 4,324,993 A | 4/1982 | Sato et al. | |
| 4,372,846 A | 2/1983 | Yamagami et al. | |
| 4,412,917 A | 11/1983 | Ahjopalo | |
| 4,413,988 A | 11/1983 | Handt et al. | |
| 4,560,472 A | 12/1985 | Granzow et al. | |
| 4,582,598 A | 4/1986 | Bilstad et al. | |
| 4,585,436 A | 4/1986 | Davis et al. | |
| 4,586,920 A | 5/1986 | Peabody | |
| 4,606,826 A | 8/1986 | Sano et al. | |
| 4,629,015 A | 12/1986 | Fried et al. | |
| 4,661,246 A | 4/1987 | Ash | |
| 4,684,460 A | 8/1987 | Issautier | |
| 4,718,890 A | 1/1988 | Peabody | |
| 4,728,433 A | 3/1988 | Buck et al. | |
| 4,747,822 A | 5/1988 | Peabody | |
| 4,767,399 A | 8/1988 | Bollish | |
| 4,769,132 A | 9/1988 | Patono | |
| 4,844,810 A | 7/1989 | Richalley et al. | |
| 4,889,635 A | 12/1989 | Chevallet | |
| 4,923,598 A | 5/1990 | Schal | |
| 4,980,054 A | 12/1990 | Lavender | |
| 4,994,026 A * | 2/1991 | Fecondini ........... A61M 1/3441 604/29 |
| 5,004,459 A | 4/1991 | Peabody et al. | |
| 5,200,090 A | 4/1993 | Ford et al. | |
| 5,211,849 A | 5/1993 | Kitaevich et al. | |
| 5,334,139 A | 8/1994 | Jeppsson et al. | |
| 5,344,568 A | 9/1994 | Kitaevich et al. | |
| 5,350,357 A * | 9/1994 | Kamen et al. ................ 604/29 |
| 5,431,626 A * | 7/1995 | Bryant et al. .................... 604/65 |
| 5,445,610 A | 8/1995 | Evert | |
| 5,643,201 A | 7/1997 | Peabody et al. | |
| 5,709,670 A * | 1/1998 | Vancaillie .......... A61B 5/02042 600/573 |
| 5,722,947 A * | 3/1998 | Jeppsson et al. ................ 604/29 |
| 5,782,796 A * | 7/1998 | Din ........................ A61M 1/28 604/27 |
| 5,938,634 A * | 8/1999 | Packard .......................... 604/29 |
| 5,938,938 A | 8/1999 | Bosetto et al. | |
| 5,956,130 A * | 9/1999 | Vancaillie .......... A61B 5/02042 356/39 |
| 5,989,423 A | 11/1999 | Kamen et al. | |
| 6,117,122 A | 9/2000 | Din et al. | |
| 6,327,895 B1 | 12/2001 | Jeppsson et al. | |
| 6,676,631 B1 | 1/2004 | Greter | |
| 6,764,761 B2 | 7/2004 | Eu et al. | |
| 7,033,539 B2 | 4/2006 | Krensky et al. | |
| 7,208,092 B2 | 4/2007 | Micheli | |
| 7,238,164 B2 | 7/2007 | Childers et al. | |
| 7,241,272 B2 | 7/2007 | Karoor et al. | |
| 7,243,893 B2 | 7/2007 | Sobue et al. | |
| 7,618,542 B2 * | 11/2009 | Okazaki ................. A61M 1/16 210/103 |
| 7,736,328 B2 | 6/2010 | Childers et al. | |
| 7,867,214 B2 | 1/2011 | Childers et al. | |
| 8,226,595 B2 * | 7/2012 | Childers et al. ................ 604/29 |
| 8,597,231 B2 * | 12/2013 | Childers et al. ................ 604/29 |
| 2004/0019313 A1 | 1/2004 | Childers et al. | |
| 2004/0215129 A1 * | 10/2004 | Edgson ................. A61L 2/0023 604/29 |
| 2006/0124548 A1 * | 6/2006 | Okazaki ................. A61M 1/16 210/646 |
| 2012/0041775 A1 * | 2/2012 | Cosentino ........... G06F 19/3418 705/2 |

FOREIGN PATENT DOCUMENTS

| | | |
|---|---|---|
| JP | 07016294 A2 | 1/1995 |
| JP | 2000-254223 | 9/2000 |
| JP | 09-508302 | 4/2006 |
| JP | 2006-512138 | 4/2006 |
| WO | WO 95/20985 | 10/1995 |
| WO | WO 96/24396 | 8/1996 |
| WO | WO 2004/060449 | 7/2004 |

OTHER PUBLICATIONS

Brochure for Gambro Serena, Baxter PD, Oct. 2005 (11 pages).
HomeChoice System "Questions & Answers" written by Baxter in Jul. 2004 (41 pages).
Brandes et al: Optimization of Dialysis Flow and Mass transfer During Automatic Peritoneal Dialysis published by American Journal of Kidney Diseases, vol. 25, No. 4 (April), 1995; pp. 603-610.
Amici et al: Role of Drain and Fill Profile in Automated Peritoneal Dialysis, Ronco c. et al (ed): Automated Peritoneal Dialysis, Contrib Nephrol. Basel, Kargar, 1999 vol. 129, pp. 44-53.
International Search Report for International Application No. PCT/US2007/069642 dated Nov. 5, 2007.
Japanese Office Action mailed Aug. 2, 2013, corresponding to Japanese Patent Application No. 2009-512300.
Japanese Office Action mailed Aug. 1, 2013, corresponding to Japanese Patent Application No. 2012-139840.
Japanese Office Action mailed May 20, 2014, corresponding to Japanese Patent Application No. P2012-139840.
European Office Action dated Jul. 21, 2015, corresponding to European Patent Application No. 07762317.1 (3 pages).
Japanese Office Action dated Feb. 16, 2016, corresponding to Japanese Patent Application No. P2015-079379 (10 pages).
Japanese Office Action dated Oct. 25, 2016, corresponding to Japanese Patent Application No. P2015-079379 (8 pages).

* cited by examiner

METHOD OF PERFORMING PERITONEAL DIALYSIS USING PNEUMATIC VALVES

PRIORITY CLAIM

This application claims priority to and the benefit as a continuation application of U.S. application Ser. No. 13/550,243, entitled "Peritoneal Dialysis System Having Heater Pan and Weight Sensor", filed Jul. 16, 2012, now U.S. Pat. No. 8,597,231, which is a continuation of U.S. patent application Ser. No. 11/420,608, entitled "Automated Dialysis System Driven by Gravity and Vacuum", filed May 26, 2006, now U.S. Pat. No. 8,226,595, issued Jul. 24, 2012, the entire contents of each of which are expressly incorporated herein by reference and relied upon.

BACKGROUND OF THE INVENTION

In general, the present invention relates to medical fluid delivery systems that employ a disposable set with sterile fluid pathways. In particular, the present invention provides systems, methods and apparatuses for disposable set-based dialysis medical fluid therapies, including but not limited to those using peristaltic pumps, diaphragm pumps, pneumatic pumps and gravity.

Due to various causes, a person's renal system can fail. Renal failure produces several physiological derangements. The balance of water, minerals and the excretion of daily metabolic load is no longer possible and toxic end products of nitrogen metabolism (urea, creatinine, uric acid, and others) can accumulate in blood and tissue.

Kidney failure and reduced kidney function have been treated with dialysis. Dialysis removes waste, toxins and excess water from the body that would otherwise have been removed by normal functioning kidneys. Dialysis treatment for replacement of kidney functions is critical to many people because the treatment is life saving.

Hemodialysis ("HD") and peritoneal dialysis ("PD") are two types of dialysis therapies used commonly to treat loss of kidney function. HD removes waste toxins and excess water from the patient's blood. The patient is connected to a hemodialysis machine via catheters into a patient's vein and artery. Blood is pumped from the patient and through the inside of hollow, porous tubes of a dialyzer connected to the machine. The machine produces dialysate, which is pumped outside the hollow, porous tubes. A pressure gradient causes excess water to be pulled from the blood, through the pores of the membrane, into the dialysate, where it is carried away. Diffusion and osmosis causes waste and toxins to move thought the pores into the dialysate to be carried away. Cleaned blood is returned to the patient. A large amount of dialysate, for example about 120 liters, is consumed to dialyze the blood during a single hemodialysis therapy. HD lasts several hours and is generally performed in a treatment center about three or four times per week.

PD uses a dialysis solution, or "dialysate," which is infused into a patient's peritoneal cavity via a catheter. The dialysate contacts the peritoneal membrane of the peritoneal cavity. Waste, toxins and excess water pass from the patient's bloodstream, through the peritoneal membrane and into the dialysate due to diffusion and osmosis, i.e., an osmotic gradient occurs across the membrane. The spent dialysate is drained from the patient, removing waste, toxins and excess water from the patient. This cycle is repeated.

There are various types of PD therapies, including continuous ambulatory peritoneal dialysis ("CAPD"), automated peritoneal dialysis ("APD"), tidal flow APD and continuous flow peritoneal dialysis ("CFPD"). CAPD is a manual dialysis treatment. The patient manually connects an implanted catheter to a drain, allowing spent dialysate fluid to drain from the peritoneal cavity. The patient then connects the catheter to a bag of fresh dialysate, infusing fresh dialysate through the catheter and into the patient. The patient disconnects the catheter from the fresh dialysate bag and allows the dialysate to dwell within the peritoneal cavity, wherein the transfer of waste, toxins and excess water takes place. The introduction of twin bag sets reduced the number of connections and disconnections by "Y-ing" the drain line and the fresh dialysate bag. Nevertheless, manual PD requires a significant amount of time and effort from the patient, leaving ample room for improvement. After a dwell period, the patient repeats the manual dialysis procedure, for example, four times per day, each treatment lasting about an hour.

APD is similar to CAPD in that the dialysis treatment includes drain, fill, and dwell cycles. APD machines, however, perform the cycles automatically, typically while the patient sleeps. APD machines free patients from having to manually perform the treatment cycles and from having to transport supplies during the day. APD machines connect fluidly to an implanted catheter, to a source or bag of fresh dialysate and to a fluid drain. APD machines pump fresh dialysate from a dialysate source, through the catheter, into the patient's peritoneal cavity, and allow the dialysate to dwell within the cavity, and allow the transfer of waste, toxins and excess water to take place. The source can be multiple sterile dialysate solution bags.

APD machines pump spent dialysate from the peritoneal cavity, though the catheter, to the drain. As with the manual process, several drain, fill and dwell cycles occur during APD. A "last fill" occurs at the end of CAPD and APD, which remains in the peritoneal cavity of the patient until the next treatment.

Both CAPD and APD are batch type systems that send spent dialysis fluid to a drain. Tidal flow systems are modified batch systems. With tidal flow, instead of removing all of the fluid from the patient over a longer period of time, a portion of the fluid is removed and replaced after smaller increments of time.

Continuous flow, or CFPD, systems clean or regenerate spent dialysate and thereby consume a lesser volume dialysate when compared to CAPD or conventional APD. Regeneration systems pump fluid into and out of the patient, through a loop. Dialysate flows into the peritoneal cavity through one catheter lumen and out another catheter lumen. The fluid exiting the patient passes through a reconstitution device that removes waste from the dialysate, e.g., via a carbon filter and a urea removal column that employs urease to enzymatically convert urea into ammonia. The ammonia is then removed from the dialysate by adsorption prior to reintroduction of the dialysate into the peritoneal cavity. Additional sensors are employed to monitor the removal of ammonia. CFPD systems are typically more complicated than batch systems.

Many PD systems use gravity to fill and drain. Patient data published by Brandes et al. shows that flow rates during fill cycle are relatively constant and related to the patient's position (supine>sit) and the absolute head height of the supply bag. Drain cycles however normally take about twice as long as fill cycles and have an antilog relationship with time. Within the drain cycle, about 80% of intra-peritoneum volume is drained within the first 40% of the total drain time.

Similar results are found from patient data by Amici et al., and from patient trials for Baxter's HomeChoice and Quantum PD cyclers.

Flow rates of gravity fill and drain are functions of several physical parameters, including head heights to the patient's peritoneum, catheter type (resistances), tubing set type, etc. To overcome the fill and drain problems, some advanced APD machines use pumps to fill and drain. Pumps provide active fluid delivery but add complexity and cost. Accordingly, a need exists to provide a relatively low cost PD machine that combines desirable aspects of different types of APD systems.

SUMMARY OF THE INVENTION

Described below is a peritoneal dialysis ("PD") system that combines the advantages of gravity dialysate delivery and pumped dialysate delivery. In particular, gravity is used to fill the patient, while a vacuum source or pump is used to drain the patient in one preferred embodiment. The vacuum source can be variable, e.g., from zero to −1.5 psig. The vacuum source enables patients to sleep on the floor, underneath the drain bag or otherwise at an elevation that would not allow for adequate drain flow via gravity.

In one primary embodiment, the system includes a stand. A heater plate is positioned at the top of the stand. The heater plate supports and heats one or more supply bag, such as one or more supply bag and a last-bag (holding an amount of dialysate that will be left in the patient between automated treatments). The stand is adjustable so that the supply bags are supported at an appropriate height above the patient, e.g., thirty-six inches. A line or tube extends from each supply bag to a valve, such as a multi-way pinch valve. The pinch valves are operated by the vacuum source. A control unit operates the vacuum source sequence. The control unit includes a microprocessor and memory in one embodiment, which control the vacuum source. The control unit also receives signals from a load cell or strain gauge, which is coupled to the drain container. This is done for the monitoring and the control of ultrafiltration which is generally considered to be the difference between the drained fluid volume and the filled fluid volume.

A patient line extends from the multi-way valve. The patient line at its distal end includes a connector that connects to a transfer set and catheter implanted into the patient. A drain line also extends from the multi-way valve. The drain line is connected to a reusable drain container, such as a rigid container. A vacuum line extends from the rigid container to the vacuum source. In one embodiment, the vacuum line is located elevationally above the level that the spent fluid will rise to in the drain container. In this configuration, fluid cannot reach the vacuum line, precluding the spent fluid from the drain container from reaching and potentially damaging the vacuum source. A hydrophobic membrane can also be placed at the interface between the drain container and the drain line for this purpose.

In this first embodiment, a priming cycle occurs as follows. The patient positions the end of the patient line so that its distal end is at substantially the same height as the supply bags. For example, the heater or its stand could include a hook onto which the patient hangs the patient line connector for priming. The control unit controls the vacuum source so that the valves to each of the supply bags, the patient line and the drain line are opened. The control unit is programmed to keep the valves open for a certain amount of time or until a certain volume (or weight) of fluid has flowed to ensure that each line is primed with fluid without dumping too much fresh fluid to drain.

In the first embodiment, a drain cycle is performed, e.g., first to remove the spent last-bag volume of fluid residing in the patient's peritoneum from the night before. Here the control unit causes the vacuum source to open the drain valve and patient line valve, keeping all supply valves closed. The control unit also causes the vacuum source to pull a vacuum on the rigid drain container, which is connected to the drain line. The vacuum pulls spent dialysate from the patient's peritoneum, through the multi-way valve and into the drain container, which fills from the bottom up via gravity. The load cell and control unit measure the weight of the fluid in the drain container. Weight changes over time are also measured to determine flow rate. The flow rate is used as feedback to control the amount of vacuum applied to the drain container, which allows the flow rate of the drain cycle to be optimized.

The control unit in one embodiment stores one or more patient profile, in which the variable vacuum source is modified to optimize flow and pressure with particular physiological characteristics of the patient. For example, when the patient's peritoneum is relatively full, the controller can be set to cause the vacuum source to remove fluid rapidly and relatively constantly from the patient. This can be done using a relatively low suction pressure because the source of spent fluid is relatively abundant and flows readily from the peritoneal cavity. As the patient's peritoneum becomes more and more empty, and the source of spent fluid becomes increasingly less abundant, the fluid flow starts to slow down. The suction pressure can be decreased to prevent the negative pressure in the patient's peritoneal cavity from causing pain to the patient. The suction pressure can be decreased from −1.5 to −1.2 psig for example. The profile is therefore adjusted to drain the patient as quickly, safely and comfortably as possible.

Next, a fill cycle occurs as follows. The control unit causes the vacuum source to close the drain valve and each of the supply bag (last-bag) valves except for the initial supply bag valve. The control unit also causes the vacuum source to open the patient line valve. Gravity forces fluid from the initial supply bag to the patient's peritoneum. The head height from the supply bag to the patient will determine the flow rate. This fill flow through 6 mm outside diameter×4 mm inside diameter tubing can reach 200 ml/min under a twenty-four inch head height and 300 ml/min under a thirty-six inch head height.

Afterwards, the control unit causes the vacuum source to close all valves for a dwell period in which the first supply of fluid resides in the patient's peritoneum, absorbing waste products.

After the dwell, the next drain cycle occurs, and so on. In the next fill cycle, a different supply bag is used. In the last fill cycle, a last-bag is used, which can contain a lesser or greater amount of dialysate, and which is intended to dwell in the patient's peritoneum until the next therapy session. Each fill and last-bag has its own dedicated control valve in one embodiment.

In a second primary embodiment, gravity is again used to fill the patient and vacuum is used to drain the patient. Here, the system includes a machine or control unit that is placed on a night stand for example above the patient, e.g., fifteen to forty inches above the patient. The top of the unit includes a load cell and a heater pan. A dual chamber bag is placed on the load cell/heater pan. The lower chamber, which resides directly on the heater pan, is a heating container or warmer pouch, which receives fresh fluid from a supply bag.

The upper chamber is a temporary drain container, which receives spent fluid pumped from the patient's peritoneum via the vacuum source. The upper, temporary drain container of the dual chamber bag is connected fluidly to a house drain or final drain container, which is located elevationally below the dual chamber bag. Spent fluid is gravity fed from the dual chamber bag to house drain.

A vacuum-tight cover is placed over the dual chamber bag. Suitable gasketing and locking mechanisms are provided so that the cover can be sealed to the unit, around the load cell and heater pan. In this manner, a vacuum can be drawn inside the cover and on the outside the dual chamber bag residing beneath the cover. The cover is configured to support one or more supply bag (including a last-bag).

The dual chamber bag includes a valve portion in one embodiment. For example, the same sheets or plies used to form the fresh and spent containers can be used to form the valve chambers and fluid pathways of the valve portion. Or, the same sheets or plies can be used with a rigid path and valve forming member to form the valve portion. In another embodiment, the dual chamber bag is connected fluidly to a separate valve cassette. In any case, the valve portion or valve cassette is operable with a valve actuation portion of the control unit. The valve actuators in one embodiment are spring actuated closed and vacuum actuated open (against the spring). In this configuration, the valves close in a failsafe manner upon power loss or vacuum source failure.

In this second embodiment, a priming cycle occurs as follows. The patient positions the end of the patient line so that its distal end is at substantially the same elevation as the one or more supply bag residing on top of the vacuum-tight cover. For example, the cover could include a hook onto which the patient hangs the patient line connector for priming. The control unit controls the vacuum source so that the valves to the fresh container of the dual chamber bag and to the patient line are opened. The control unit is programmed to keep these valves open for a certain amount of time or until a certain volume of fluid has gravity flowed to ensure that the fresh container and patient line are primed with fluid. The dual chamber bag weight is measured and recorded.

Next, a drain from the patient's last-bag fill from the night before occurs, while the fill volume in the fresh container of the dual chamber bag via the prime is heated. Here, the control unit causes the vacuum source to: (i) open a plurality of valves so that spent fluid can flow from the patient to the spent container of the dual chamber bag (for weighing); and (ii) pull the last-bag spent fluid from the patient, e.g., at −1.5 psig under the vacuum-tight cover, against the head height difference between the temporary spent container of the dual chamber bag and the patient. The volume of fluid pulled from the patient is weighed and known.

Once the fresh fluid is heated to a desired temperature and all spent last-bag fluid is pulled from the patient, the weigh scale and control unit record the combined weight of the fluid in the dual chamber bag. Then, the fill cycle starts and the heated fresh fluid is gravity fed to the patient. Here, the control unit causes the vacuum source to open one or more valve, enabling heated fluid from the fresh container of the dual chamber bag to be gravity fed to the patient's peritoneum.

The line from the fresh container of the dual chamber bag to the patient is located at the bottom of the bag, such that air egressing from the heated fluid floats to the top of the fresh container and only heated fresh fluid flows from the fresh container to the patient. In an alternative embodiment, an integral air separation chamber is provided in communication with the fresh container to collect air egressing from the heated fluid. As fluid exits the heated supply bag, the weigh scale or load cell weighs and records the amount of fluid that has been delivered to the patient, which is seen as the loss in weight in the dual chamber bag from the total combined weight of the dual fills described previously. Once the programmed volume of fluid is delivered the patient or the scale no longer senses a drop in weight, the fill to the patient portion of the fill cycle is completed, one or more valve is closed, and the weight remaining in the dual chamber bag is recorded by the weigh scale and control unit. The control unit calculates the drain and fill volumes by subtracting the pre- and post-scale weights for both drain and fill cycles.

After completion of the fill-to-patient portion of the fill cycle, the control unit causes the vacuum source to close at least the patient and drain valves for a dwell period in which the first supply of fluid is allowed to reside in the patient's peritoneum, absorbing waste products through diffusion and osmosis. During the dwell period, the control unit causes the vacuum source to open one or more valve, enabling fluid from the same or different dextrose supply bag to refill the fresh container of the dual chamber bag, so that it can be preheated for the next fill-to patient cycle. The increase in weight is again recorded. If it has not already happened, the control unit can also cause the vacuum source to open one or more valve, enabling the initial spent last-bag fluid to be gravity fed from the temporary drain chamber of the dual chamber bag to the final drain container or house drain.

After the dwell, the next drain cycle occurs, wherein the vacuum source pulls spent fluid from the patient against the head height difference to the temporary spent container of the dual chamber bag. The incremental gain of weight due to the fluid reaching the temporary spent container is recorded. As soon as the first fill of spent fluid is pumped from the patient, the newly heated fresh fluid can be gravity fed from the fresh container of the dual chamber bag to the patient. The incremental loss in weight is recorded as the second fill volume. If the supply bags contain the prescribed fill volume, the recorded and prescribed volumes serve to double-check one another.

Next, the second dwell period begins and the above-described process is repeated. Eventually a last-bag volume of fresh dialysate is delivered to the patient, which is allowed to dwell in the patient until a new therapy is begun the next day or evening.

Either primary embodiment can be run to perform full fill, dwell and drain cycles or perform same partially, e.g., in a tidal mode type of modality. In the end a difference in the amount of fluid removed from the patient versus the amount of fluid delivered to the patient is calculated and represents ultrafiltrate or UF. The UF therapy prescription is set so that at the end of treatment the patient reaches his or her "dry weight". The twenty-four hour UF calculation uses the last-bag volume from the night before and thus involves filling and draining from two treatments.

It is therefore an advantage of the embodiments described herein to provide an improved dialysis system.

It is another advantage of the embodiments described herein to provide a gravity fill dialysis system for patients who sleep on the floor or low to the ground.

It is a further advantage of the embodiments described herein to provide a gravity fill dialysis system employing simplified pneumatics and/or hydraulics.

It is yet another advantage of the embodiments described herein to provide a gravity fill dialysis system that employs a simplified disposable set or unit.

It is yet a further advantage of the embodiments described herein to provide a gravity fill dialysis system that can be adapted for different therapy modalities.

It is still another advantage of the embodiments described herein to provide a gravity fill dialysis system that is relatively gentle on the patient.

It is still a further advantage of the embodiments described herein to provide a gravity fill dialysis system that achieves maximum flowrates, allowing for maximum dwell times and clearances.

Moreover, it is an advantage of the embodiments described herein to provide gravity fill, vacuum drain dialysis system.

Additional features and advantages of the present invention are described in, and will be apparent from, the following Detailed Description of the Invention and the figures.

DETAILED DESCRIPTION OF THE INVENTION

Figure 1:
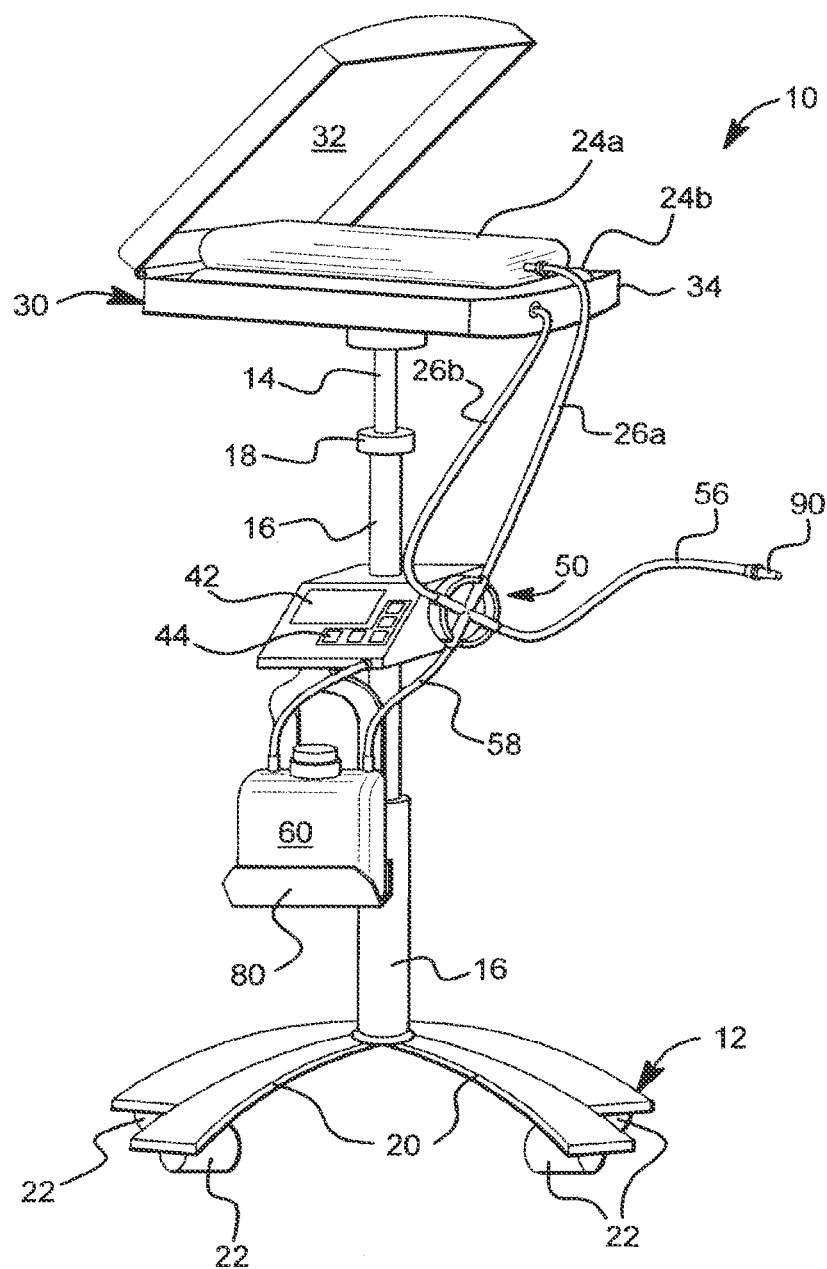
FIG. 1 is a perspective view of one primary embodiment of an automated peritoneal dialysis system driven by gravity and vacuum.
Figure 2:
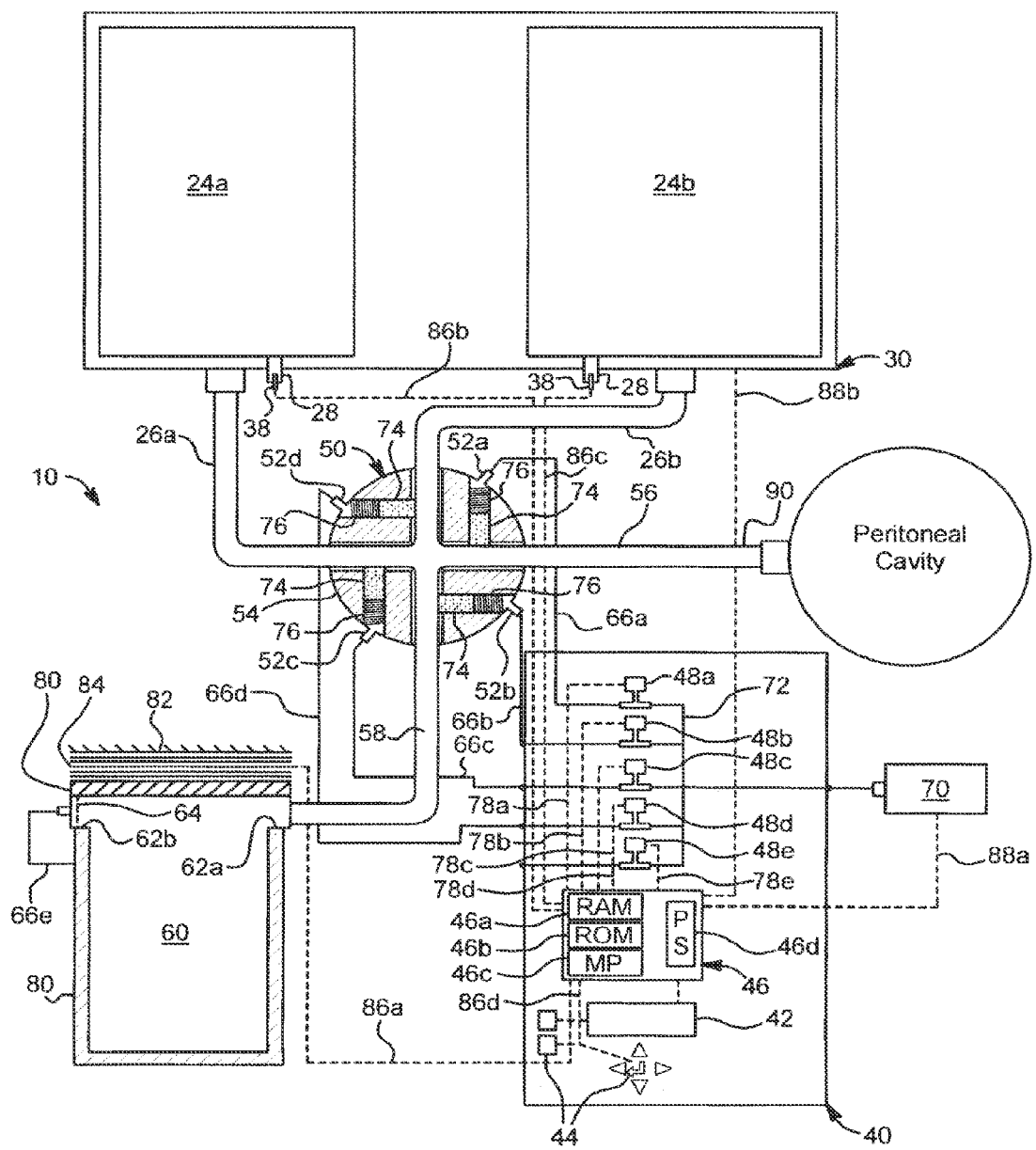
FIG. 2 is a schematic view of one embodiment for the disposable portion, valve, vacuum lines, electrical lines, control unit and control scheme of the system shown in FIG. 1.
Figure 3:
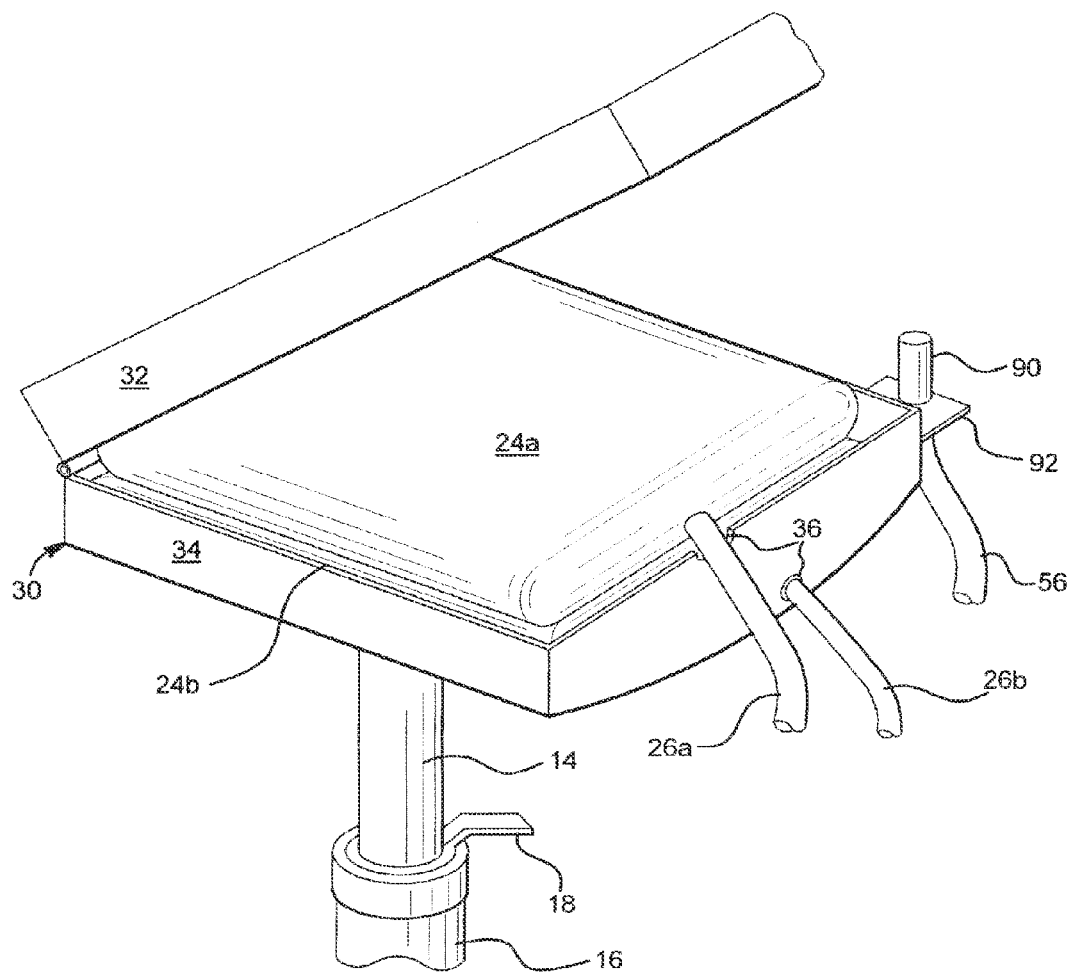
FIG. 3 is a perspective view of one embodiment for the heater and associated stand of the system shown in FIG. 1.

Referring now to FIGS. 1 to 3, a first primary embodiment of an automated peritoneal dialysis ("APD") system is illustrated by system 10. System 10 includes an adjustable stand 12, which in an embodiment is made of a relatively strong, lightweight and low cost metal or hard plastic. Stand 12 can for example be aluminum, steel or some combination of metal and plastic. Adjustable stand 12 includes an inner tube or stem 14. Inner tube or stem 14 is sized to slide within an outer tube 16. The patient or caregiver sets the overall height of stand 12 by moving inner tube 14 up or down with respect to outer tube 16 to a desirable position. Afterward, the patient or caregiver locks the inner tube in place relative to outer tube 16 via a suitable locking mechanism 18. Outer tube 16 is fastened to, welded to or formed integrally with a set of legs 20, which hold and balance tubes 14 and 16 and the apparatuses connected thereto. Casters or wheels 22 are coupled at the ends of legs 20, so that system 10 can be maneuvered easily. One or more of casters 22 can have a locking mechanism to lock system 10 at a desired location.

As seen more closely in FIG. 3, inner tube 14 is connected to and supports a medical fluid heater 30. Medical fluid heater 30 can use any mode of heat transfer suitable to heat liquid within one or more medical fluid supply bag, such as resistance plate heating, radiant heating, convective heating, and any suitable combination thereof. Heater 30 in the illustrated embodiment includes a clam shell construction having a lid 32 and a base 34. In an embodiment, the heater elements and associated heating are located in base 34. Alternatively, the elements or heating pads are located in lid 32. Further alternatively, the heating elements or pads are located in both lid 32 and base 34.

In the illustrated embodiment, heater 30 is sized and configured to hold a pair of supply bags 24a and 24b, such that one supply bag 24a rests on top of the second supply bag 24b. A single supply bag is provided alternatively. Further alternatively, three or more supply bags 24 (referring collectively to supply bags 24a, 24b, etc.) are provided. One of supply bags 24 can be a last bag that holds a last-bag volume of fluid that remains at the end of treatment in the patient's peritoneum until the next treatment. Heater 30 can alternately hold two supply bags placed side by side with a third bag placed optionally on top of and between the bottom two bags.

As illustrated, base 34 defines one or more opening and/or notch 36. Openings 36 enable supply tubes 26a and 26b to extend from supply bags 24a and 24b, respectively, while enabling lid 32 and base 34 to be closed together tightly around bags 24a and 24b. This configuration helps to prevent supply tubes 26a and 26b from becoming crimped.

As seen in FIG. 2, supply bags 24a and 24b can include or define one or more port 28, which is configured to accept a temperature sensing device 38 in a sealed manner. Temperature sensing device 38 can be any suitable device, such as a thermistor, thermocouple or resistance temperature device ("RTD") sensor. In the illustrated embodiment, temperature sensing devices 38 measure the temperature of heated dialysis directly. That is, temperature sensing devices 38 actually contact the dialysate. In an alternative embodiment, the temperature sensing devices 38 are located for example on one or more of the inner surfaces of lid 32 and base 34 and contact the bag material instead. Here, the temperature of the bag material is assumed to reach the temperature of the dialysate over time. Alternatively, if a slight difference between bag and dialysate temperature is always present, that difference can be determined and compensated for.

FIG. 1 shows that outer tube 16 supports a control unit 40. Control 40 includes a video monitor 42, such as a liquid crystal display ("LCD"), or other suitable type of display. Video monitor 42 in an embodiment operates with a touch screen overlay (not illustrated), which enables the operator to input commands into control until 40. Alternatively, control unit 40 includes off-screen input devices 44, which can be membrane switches, knobs, push-buttons or other types of electromechanical input devices.

As seen in FIG. 2, video monitor 42 and input devices 44 are connected and controlled by one or more printed circuit board 46, which includes among other components random access memory ("RAM") 46a, read only memory ("ROM") 46b, a microprocessor 46c and a power supply 46d. Code and data are stored on ROM 46b and RAM 46a as is known in the art. Processor 46c cooperates with RAM 46a and ROM 46b to control each of the functions of system 10, such as control of heater 30, the control of ultrafiltration removal and the control of the valves of system 10 via electrical solenoids 48a to 48e. Alternatively or additionally, control unit 40 controls those functions using an application specific circuit ("ASIC"), solid state relay, MOSFET and the like. Power supply 46d provides the necessary power (amount and type) to solenoids 48a to 48e and heater 30. To the extent that system 10 includes components requiring different types or ranges of power, a plurality of power supplies, such as power supply 46d, can be provided.

Solenoids 48a to 48d control valves 52a to 52d, respectively, of multi-way valve assembly 50 via vacuum lines 66a to 66e, respectively. Valve assembly 50 in an embodiment includes a housing 54, which defines or provides chambers for valves 52 (referring collectively to valves 52a to 52d). Housing 54 can be made of plastic or metal as desired. Valve assembly 50 can be attached to or integrated with the housing of control unit 40.

Figure 4:
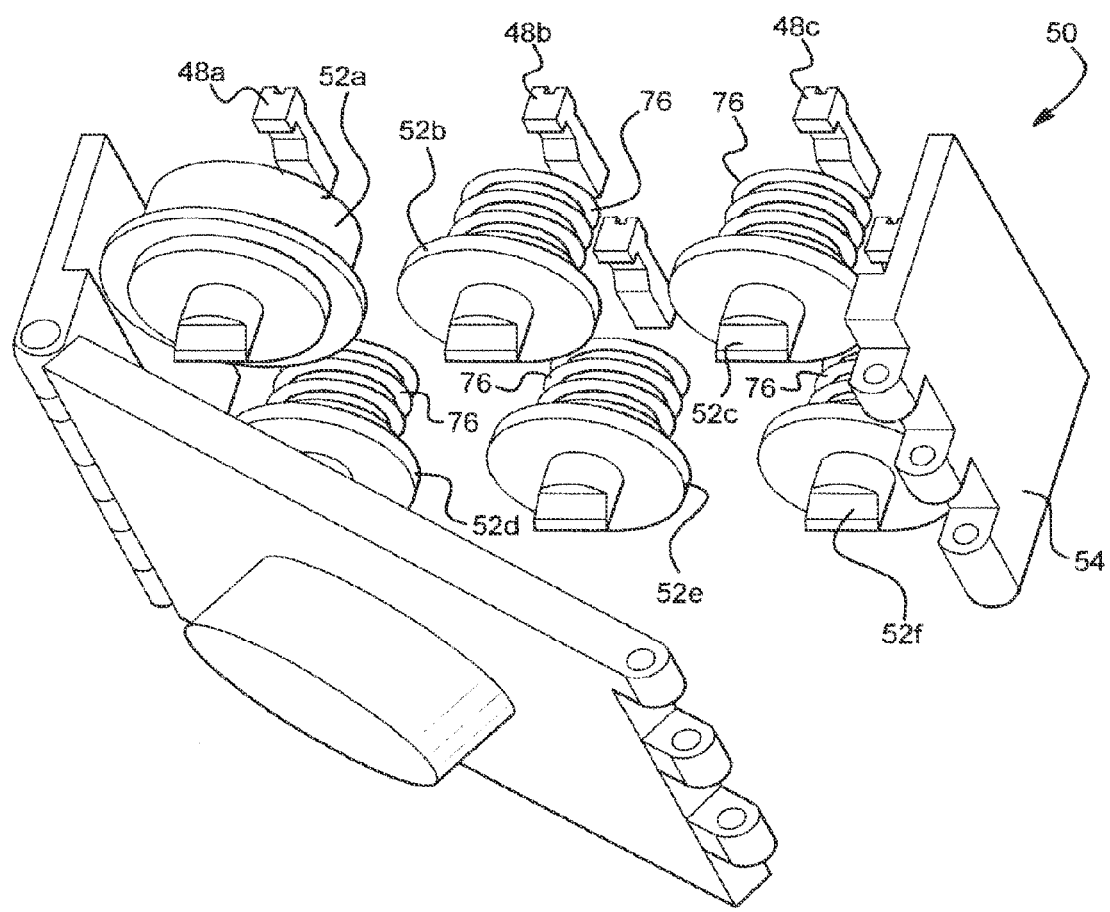
FIG. 4 is a perspective view of one embodiment of a multi-tube valve actuator used with the automated peritoneal dialysis system driven by gravity and vacuum.

FIG. 4 illustrates one suitable configuration for multi-way valve assembly 50. Here, valve assembly 50 is a custom manufactured assembly that is integral with the door of control unit 110 and allows the tubing set (FIG. 15) to be loaded for treatment. Valve assembly 50 provides six pinch valves 52a to 52d (only four used in FIG. 2). Springs 72 push valve heads to pinch a tube closed. A vacuum is applied to compress springs 76 and open a fluid pathway. In FIG. 4, solenoids 48a to 48f are mounted with multi-way valve assembly 50. Solenoids 48a to 48f operate as described below in connection with FIG. 2.

In FIG. 2, multi-way valve assembly 50 operates directly with supply lines 26a and 26b, a patient line 56 (which is connected to a port coupled to the patient, the patient port coupled fluidly to a catheter that extends inside the patient to the patient's peritoneal cavity). A fourth drain line 58 runs from the multi-way connection within valve assembly 50 to a drain container 60.

Drain container 60 includes a spent fluid inlet 62a, which is coupled to drain line 58. Drain container 60 also includes a spent fluid outlet 62b which is coupled to a fifth vacuum line 66e. A hydrophobic membrane 64 is placed in outlet 62b of drain container 60 in one embodiment to preclude spent fluid from entering vacuum line 66e. Also, as seen in FIG. 2, inlet 62a and outlet 62b of drain container 60 are placed elevationally at the top of drain container 60, such that spent fluid entering inlet 62a tends to fall via gravity to the bottom of drain container 60 and fill the drain container upwardly. Thus the configuration of drain container 60 itself tends to preclude spent dialysate from entering vacuum line 66e.

A vacuum source 70 is connected to the inlet ends of solenoids 48a to 48e via a vacuum manifold 72. Vacuum source 70 and manifold 72 are configured to maintain a negative pressure on the inlet ends of solenoids 48a to 48e at all times while vacuum source 70 is powered. Vacuum source 70 in one embodiment includes a vacuum regulator and vacuum pump combining to provide a variable vacuum output, which can supply a negative pressure to valves 52a to 52d and drain container 60 from anywhere between zero psig up to −1.5 psig and beyond. One suitable vacuum regulator for vacuum source 70 is an ITV 209 model electronic vacuum regulator provided by SMC Corporation of America, Indianapolis, Ind. The regulator is placed upstream of the vacuum pump in one embodiment.

In the embodiment illustrated in FIG. 2, valves 52a to 52d are spring loaded, failsafe valves. Valves 52a to 52d each include a plunger 74 which is compressed via a spring 76 to pinch or close off patient line 56, drain line 58, supply line 26a and supply line 26b, respectively. To open one or more of those lines, a vacuum or negative pressure is applied to the valve source 70, manifold 72, the opening of one or more electrically operated solenoid 48a to 48e, and the appropriate vacuum line 66a to 66d. Valves 52a to 52d are said to be failsafe because upon a power loss or loss of vacuum, springs 76 cause each of the plungers 74 to close their respective tube or line, precluding any further flow of fresh or spent dialysate.

PCB 46 controls electrically operated solenoids 48a to 48e in an embodiment by sending on/off electrical signals to the solenoids over electrical lines 78a to 78e, respectively. The program stored on controller or PCB 46 causes electrical signals to open one or more of solenoid valves 48a to 48e at an appropriate time to establish a desired vacuum flow path and/or draw a vacuum on drain container 60.

As seen in FIGS. 1 and 2, drain container 60 is supported by a scale 80. Scale 80 in turn is connected to mechanical ground 82 via a load cell or strain gauge 84. Load cell or strain gauge 84 sends a signal to controller or PCB 46 via a signal line 86a. The signal from strain gauge 84 can be for example a variable 4 to 20 milliamp or 0 to 10 VDC signal, which varies depending upon the amount of spent fluid that has been pulled by vacuum to drain container 60. If the strain gage is bumped, an incorrect weight signed will be produced momentarily. Controller or PCB 46 can include averaging routines in its software that accommodates these anomalies. An accelerometer can be attached to the load cell, so that the controller will know when the load cell has been bumped. Anomalous readings are then excluded from the averaging routines. Similar variable signals are also sent from temperature measuring devices 38 along lines 86b and 86c, respectively, to controller or PCB 46. Controller 46 also receives inputs (e.g., on/off) from manually operated input devices 44 via input signal lines 86d.

On the output end, besides output lines 78a to 78e (e.g., on/off) to solenoids 48a to 48e, respectively, controller 46 controls variable vacuum source 70 via a variable signal along output line 88a. Controller 46 further controls the output to heater 30 via a variable signal along outlet line 88b. In another embodiment, the outlet to heater 30 is an on/off type output, which is varied in frequency to control a duty cycle of heater 30.

Control unit 40 of system 10 is configured to optimize the rate at which fluid is removed from the patient's peritoneal cavity. Here, the rate at which the weight of fluid within drain container 60 changes over time is determined by dividing the difference in the signals sent by the strain gauge 82 along signal line 86a to controller 46 by a corresponding difference in time. The rate can be compared to an optimal rate stored in controller 46. The signal from controller 46 along variable output line 88a to variable vacuum source 70 is then adjusted to adjust the amount of vacuum supplied along vacuum line 66e to drain container 60. The vacuum is adjusted so that the actual rate of change of ultrafiltrate weight measured via strain gauge 84 meets the optimal drain or ultrafiltrate removal rate.

In operation, system 10 initially performs a priming cycle. Here, the distill end 90 of patient line 56 is fixed at an elevational level that is at least substantially the same as supply bags 24*a* and 24*b*. FIG. 3 shows one embodiment for doing so, in which a clip or latch 92 is fixed to the base 34 of heater 30 and is configured to hold the end 90 of patient line 56 at a height that is at substantially the same as the height of supply bags 24*a* and 24*b*. After the patient fixes patient line 56 as just described, the patient presses an input 44. Control unit 40 causes each of valves 52*a* to 52*d* to be opened at an appropriate time to enable fresh dialysate to flow through each of supply lines 26*a* and 26*b*, patient line 56 and drain line 58, flushing air from those lines.

Because fluid flow through patient line 56 is driven by gravity, the dialysate does not flow above end 90 positioned at the same elevation as supply bags 24*a* and 24*b*. The prime cycle can be configured such that controller 46 of control unit 40 causes valves 52*a* to 52*d* to be opened for a preset amount of time or alternatively until a preset volume of fluid is sensed to have flowed through the tubes, after which all valves close in one embodiment. The closure of the lines at valve assembly 50 prevents fluid from flowing out the distal open end of the lines, e.g., at inlet 62*a* of drain container 60 of drain line 58, due to the weight of the fluid column. The small inside diameter of the tubing used for the lines precludes air from flowing up into the tubing to relieve a vacuum that is created by the weight of the fluid column. Further, the closed valve assembly does not allow leakage of fluid.

After prime, in one sequence of operation, system 10 performs an initial drain sequence in which spent dialysate left over from the previous therapy is removed initially from the patient's peritoneal cavity. To do so, the patient removes the primed end 90 of patient line 56 from clip 92 of heater 30. The patient connects the end 90 to a port stitched into the patient as is known in the art. The patient then presses an input 44 indicating that therapy can begin. For the initial drain, controller 46 of control unit 40 causes solenoids 48*a* and 48*b* to open. A corresponding vacuum is supplied via vacuum lines 66*a* and 66*b* to valves 52*a* and 52*b*, respectively, to open those valves (pull them closed against the spring force). No vacuum is supplied to valves 52*c* and 52*d*, so that the corresponding springs 76 cause the corresponding plungers 74 to pinch close both supply lines 26*a* and 26*b*.

Simultaneously, controller 46 causes solenoid 48*e* to open, which in turn allows a vacuum to be drawn along vacuum line 66*e*, through hydrophobic membrane 64, and into the chamber of drain container 60. The vacuum in drain container 60 pulls fluid from the patient's peritoneal cavity, through patient line 56, through drain line 58 and into container 60, where it begins to fill to the container. As discussed above, feedback from strain gauge 84 cooperates with controller 46 and variable vacuum source 70 to optimize the rate at which fluid is pulled from the patient to drain container 60. Because the patient drain is done via vacuum, the patient can be at a lower elevational level than drain container 60, at the same level, or at a higher elevational level than drain container 60 that would nevertheless not be sufficient to drain the patient efficiently via gravity.

The drain cycle in one embodiment is performed using a profile, which optimizes the flow of fluid from the patient's peritoneum to drain container 60 to ensure that the patient is maintained in a comfortable state. To do so, drain flowrate is calculated from volume measurements in one embodiment to determine when the patient may be susceptible to discomfort. For example, the profile could divide the drain cycle into two phases, one which is a higher flow phase and another which is a lower flow phase. When the patient reaches the lower flow phase, the vacuum is adjusted to account for discomfort, which may occur at that lower flow.

Figure 5:
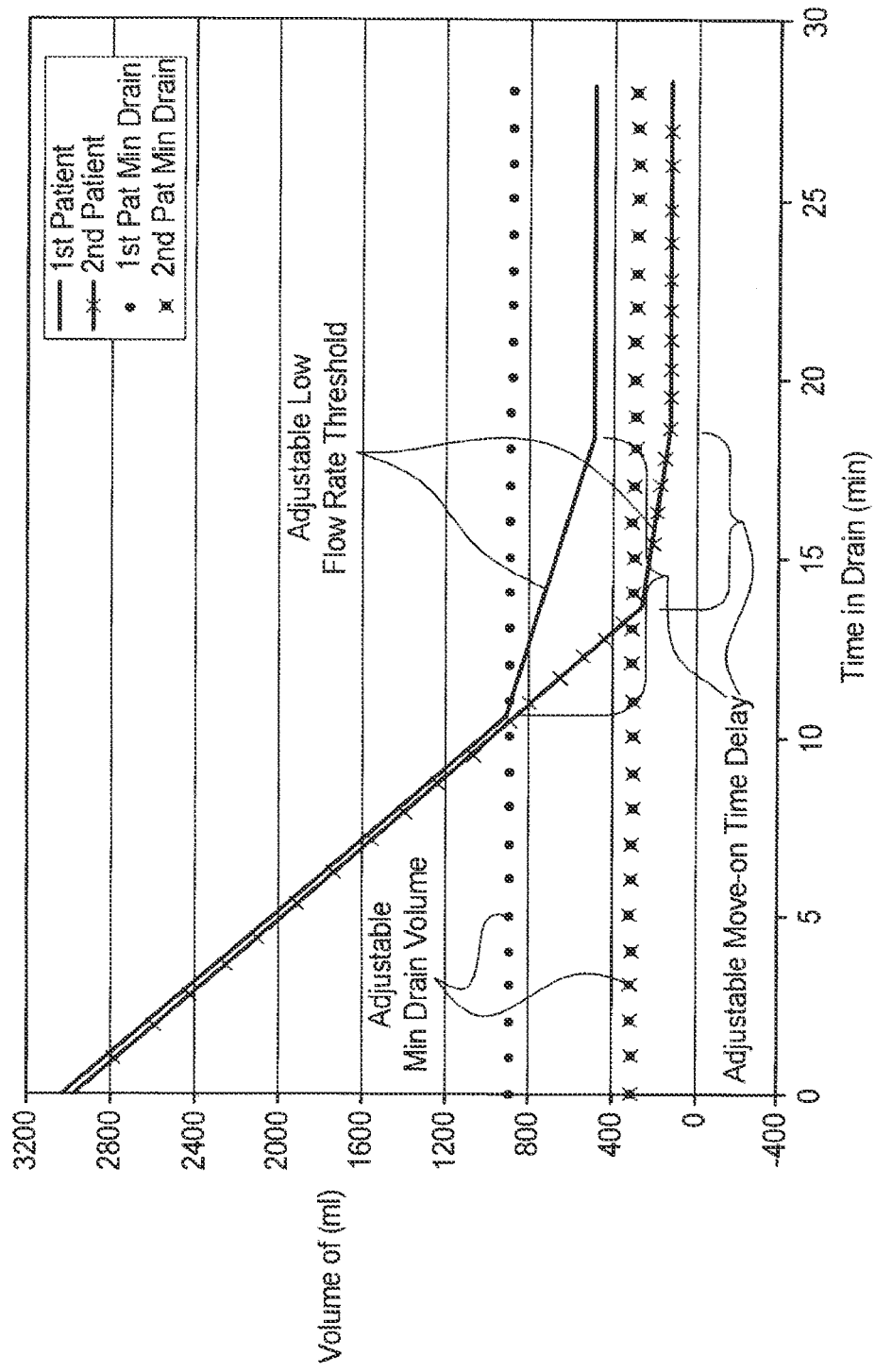
FIG. 5 is a diagram showing the volume of fluid drained versus time of drain cycle for two patients.

At the beginning of the drain cycle, the high flow phase can be performed using a relatively low suction pressure because the source of spent fluid is relatively abundant and flows readily and smoothly from the patient's peritoneal cavity. As the patient's peritoneum becomes more and more empty, and the source of spent fluid becomes increasingly less abundant, the drain flow starts to slow down. FIG. 5 illustrates the "break point" concept that is understood in the art as a change in drain flow rate, which indicates that the peritoneum is relatively empty. System 10 then decreases the suction pressure to prevent it from causing pain to the patient. For example, the suction pressure is decreased from −1.5 psig to −1.2 psig. The profile is in this way adjusted to drain the patient as quickly, safely and comfortably as possible.

Each patient can vary in terms of when the low flow phase occurs and how far the drain flowrate drops. For example, one patient may transition from the high flow phase to the low flow phase after 70% of their fill volume has been drained, whereas another patient may not transition until 90% of their fill volume has been drained. Also, the first patient's flow rate may drop to below 50 ml/min, while the second patient's flow rate may drop to below 25 ml/min when reaching the low flow phase.

The chart of FIG. 5 illustrates how patient drain rates can vary. Here, the initial drain rates for two patients are constant and track closely together for the first ten minutes of the drain cycle. At this time, and at a remaining volume of about 900 ml, the first patient's drain rate slows considerably over a "move-on" time of about eight minutes, at which point the drain cycle is stopped with approximately 550 ml of fluid remaining in the patient's peritoneum. The higher drain rate for the second patient on the other hand continues to about 13.5 minutes. At this time, and at a remaining volume of about 300 ml, the second patient's drain rate slows considerably over a "move-on" time of about five minutes, at which point the drain cycle is stopped with approximately 150 ml of fluid remaining in the patient's peritoneum.

Based on the above-described physiological characteristics of the patient, the transition in suction pressure is made based upon a combination of flowrate and volume of fluid drained. Also, the "move-on" time needs to be adjusted so that the patient does not unduly waste therapy dwell time attempting to drain the last drop of spent fluid.

The first fill cycle is then performed. In one embodiment, the fill cycle begins automatically after the initial drain, so that the patient can be asleep during this portion of the therapy if desired. In the fill cycle, controller 46 of control unit 40 causes either solenoid 48*c* or 48*d* to open, enabling a vacuum to open one of supply lines 26*a* or 26*b* via a respective valve 52*c* or 52*d*. Also, controller 46 causes solenoid 48*a* to open, enabling a vacuum to open patient valve 52*a*. Fresh dialysate is then enabled to flow from one of the supply bags 24*a* or 24*b*, through the interface at multi-way valve assembly 50, through patient line 56, and into the peritoneal cavity of the patient. The flow of fluid in the patient fill is performed via gravity. Accordingly, supply bags 24*a* and 24*b* should be set via tubes 14 and 16 and locking device 18 to be at a minimum head height distance above the patient's peritoneal cavity, such as 3 ft. (0.9 m) above the peritoneal cavity. Assuming an inner diameter of 4 mm for supply lines 26*a* and 26*b* and patient line 56, the gravity fed flow of dialysate will reach over 200 ml/min and could reach as high as 300 ml/min.

After the known amount of fresh fluid is delivered to the patient, a dwell cycle occurs in which the fresh fluid is allowed to dwell within the patient's peritoneum, while diffusive and osmotic forces remove waste and excess water from the patient. The dwell period can be varied as needed but generally lasts for one to two hours depending upon the dialysis therapy prescription. After the dwell cycle occurs, the above, drain, fill and dwell cycles are repeated one or more times as prescribed by a physician. The final fill can be performed using a last-bag, which delivers a final amount of fluid to the patient. That final amount of fluid resides within the patient's peritoneal cavity until the next time therapy is performed. System 10 also includes one or more pressure and/or flow sensor used for alarm purposes, e.g., to detect a kinked or detached line. The pressure/flow sensor can be configured to sense the pressure/flow of at least one of the patient line, the drain line, the supply line and any one of the vacuum lines/manifold.

At the end of therapy, the total amount of fluid collected in container 60 is known. Further, the total amount of fluid delivered from supply bags 24a and 24b, assuming all fluid is delivered from the supply bags to the patient, is also known. The additional weight of spent fluid in container 60 over that delivered from supply bags 24 to the patient is known as ultrafiltrate, which is the excess fluid or water that is retained by the patient between treatments due to renal failure. Because a good portion of the fluid within container 60 is from the previous therapy's last-bag or last fill, the twenty-four hour ultrafiltrate volume takes into account the previous night's volume of last fill, which is typically close or equal to the last-bag fill of the instant therapy.

In an embodiment, the connection of drain line 58 and vacuum line 66e to inlet and outlet 62a and 62b, respectively, of drain container 60 is done via a quick disconnect or other readily assembled and disassembled connection. This is done so that the patient or caregiver in the morning or otherwise after therapy can disconnect drain container 60 readily from those lines to pour its contents into a house drain, such as a toilet. Scale 80 is accordingly configured such that drain container 60 can be removed from and reloaded into same readily.

Referring now to FIGS. 6 to 19, a second primary embodiment of a system driven by gravity and vacuum is illustrated by system 100. System 100 includes many of the same components as does system 10. Where possible, these components are numbered the same. For example, system 100 includes a patient line 56 having a distill end 90. System 100 also includes a drain line or tube 58. System 100 further includes one or more supply bag 24 (referring generally to one of supply bags 24a, 24b, etc.). Supply bag 24 communicates fluidly with a supply line 26. System 100 differs in one respect from system 10 in that the load cell measures both the volume fluid that is delivered to the patient and the volume of fluid that is drained from the patient.

System 100 also includes valves that allow fluid to flow to a desired destination during a particular cycle during therapy. The valves in one embodiment are failsafe, spring/vacuum actuated valves, such as valves 52a to 52d shown in connection with FIG. 10. Those valves are located inside of a control unit 110 of system 100. The valves within control unit 110 include a spring actuator, such as spring 76 and plunger or pincher, such as plunger 74 of system 10. The opening and closing of the valves of system 100 in one embodiment is the same as that described above in connection with system 10. Accordingly, it is not necessary to re-illustrate, show or re-describe such operation.

Similarly, system 100 includes a heater 130 and load cell 184. Heater 130 can be of any of the types of fluid bag warmers described above for heater 30. Heater 130 in system 100 however is located on the top of control unit 110. The heater pan is placed on or is incorporated with a load cell 184. Load cell 184 performs the same function in system 100 as strain gauge 84 of system 10. That is, load cell 184 measures the weight of fluid pulled by vacuum into a dual chamber bag 120. Here additionally, load cell 184 measures the weight of fresh dialysate supplied to the patient. Load cell 184 in system 100 is configured to send a signal to a controller or PCB (configured with each of the alternatives described above for PCB 46) located within control unit 110 based on a compressive force due to the weight of fluid within dual chamber bag 120 (in the illustrated embodiment of system 10, strain gauge 84 provides a signal based on a tensile force applied to scale 80 via the weight of fluid drawn into control container 60). Thus while heater 130 and load cell 184 provide similar functions as heater 30 and load cell 84, their physical configuration and operation are different.

As illustrated, control unit 110 includes input devices 44 and a video monitor 42 as described above in connection with control unit 40 of system 10. The electrical layout of FIG. 2 for system 10 is also largely applicable to the electrical layout of system 100, which is housed inside control unit 110. That is, a PCB including RAM, ROM, a microprocessor (ASIC or MOSFET) and one or more power supply receives varying amperage or voltage signals from load cell 184 and one or more temperature measuring device (not illustrated), which measures the temperature of fresh dialysate located within a fresh container 122 of dual chamber bag 120 directly or at the outer surface of bag 120 directly adjacent to the heated supply within fresh container 122.

The electrical scheme of system 100 also includes a variable electrical output to a variable vacuum source (similar to that provided along line 88a to variable vacuum source 70 of system 10 shown in FIG. 2). Moreover, the controller or PCB of system 100 sends a variable or duty cycle output to heater 130 (as is done in connection with controller 46 and heater 30 of system 10). Control unit 110 in an embodiment houses electrically actuated solenoids (such as solenoids 48a to 48e of system 10), which allow or disallow a vacuum to be applied along vacuum lines (such as lines 66c to 66e of system 10) to the valves (described above) and to a vacuum chamber established beneath a vacuum tight cover 102 (shown in FIGS. 8A, 8B, 18 and 19). System 100, like system 10, includes necessary vacuum lines, which in an embodiment are housed inside control unit 110.

Cover 102 is sealed via seal 104 located around the outside of load cell 184 and heater 130 to the top of control unit 110. Seal 104 can be a soft rubber or sponge rubber seal, for example neoprene rubber or closed cell sponge silicone rubber. Seal 104 could also be constructed of an elastomer, which is extruded or molded in a geometric shape that seals well under a vacuum. A V-shaped gasket with its open side facing atmospheric pressure is one example of a suitable geometric vacuum seal. The weight of the cover may be sufficient to hold the cover in place. Clamping devices 106, such as spring loaded twist clamps, can also be provided to hold cover 102 in a sealed relationship with the top of control unit 110. In an embodiment, hinges 108 are provided such that cover 102 swings hingedly up from the top of control unit 110. The weight of fluid within supply bag 24 also helps to seal cover 102 against the top of control unit 110. That weight may be enough to maintain the seal under the relatively low negative pressures used in system 100, e.g., on the order of between 0 and −1.5 psig. Also, the negative pressure itself would tend to pull lid 102 into the gasket 104, precluding the need for clamping devices 106 and/or hinges 108.

System 100 can also include a reusable drain container or disposable drain bag (not illustrated and referred to hereafter as drain container for simplicity), which connects to and communicates fluidly with drain line 58. In system 100 however the drain container is not weighted and is not used in the same way as in system 10 to determine and control ultrafiltration removal. The drain container of system 100 here is used to collect spent dialysate. It is configured to be located beneath control unit 110, so that spent fluid from spent container 124 of dual chamber bag 120 can be gravity fed to the drain container.

Figure 9:
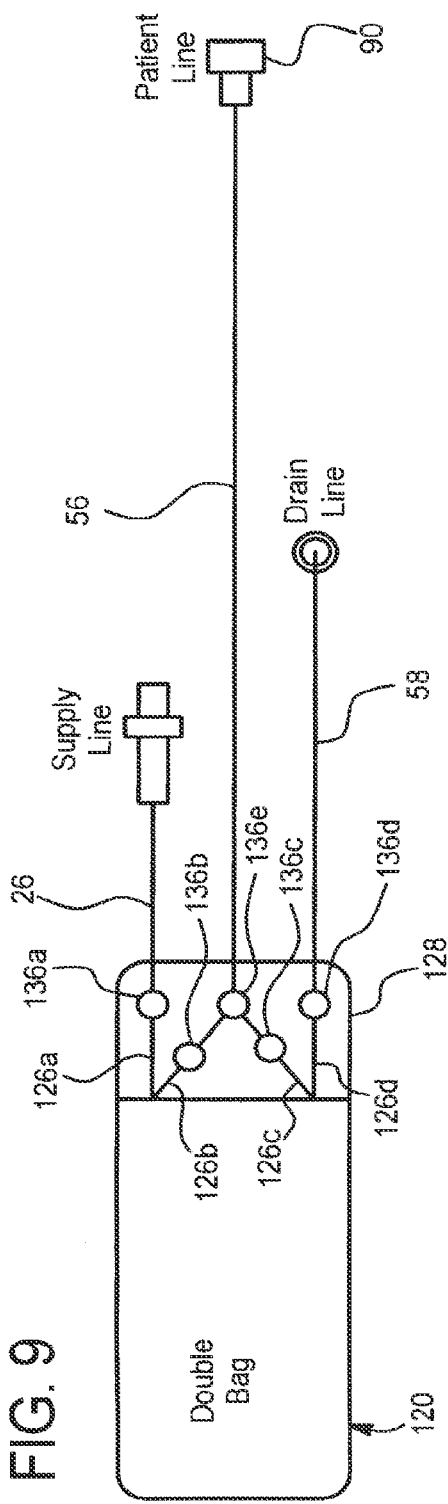
FIG. 9 is a top view of one embodiment for a disposable weigh/supply bag including a valve portion and associated tubes of the system shown in FIG. 6.
Figure 10:
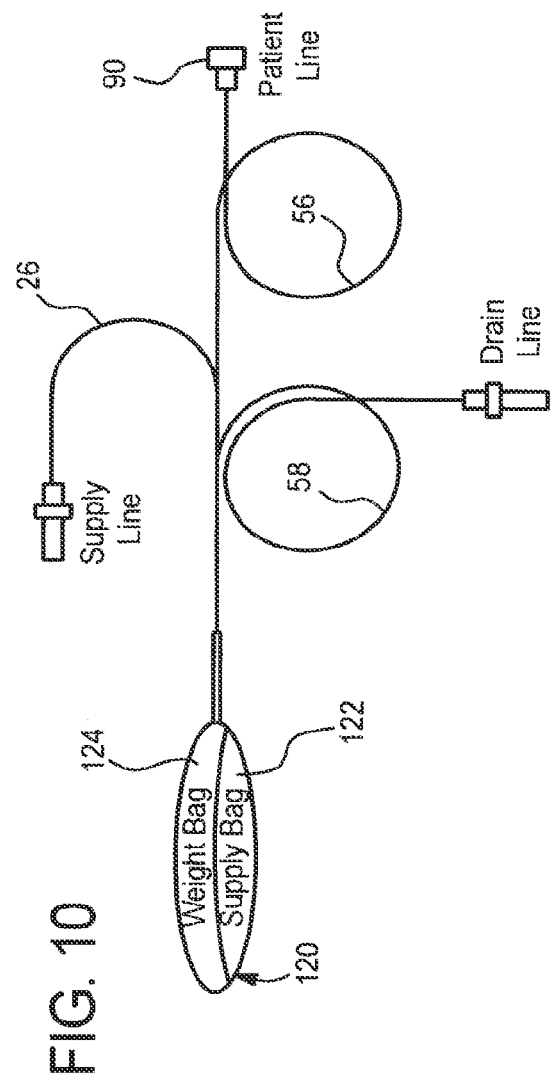
FIG. 10 is a side view of the disposable weigh/supply bag, valve and tubes of FIG. 9.

The control of fluid volume removed and flowrate is done using dual chamber bag 120, load cell 184 and the switching of valves (which are spring closed and vacuum opened in one embodiment as described above in connection with valves 52a to 52d of FIG. 10). As seen in FIGS. 9 and 10, dual chamber bag 120 includes a heated container 122 and a temporary spent container 124. In an embodiment, flexible membranes used to form heating supply and temporary drain bag containers 122 and 124, respectively, of dual chamber bag 120 are also used to form at least a portion of valve portion 128. Flow paths 126a to 126d for example can be thermal formed and one of the upper or lower plies of dual chamber bag 120. In an alternative embodiment, two of the plies used to form containers 122 and 124 are sealed to a rigid member to form valve portion 128. Further alternatively, valve portion 128 is separate from bag 120 and connected fluidly thereto via separate tubes forming part of flow paths 126a to 126d.

Flow paths 126a to 126d each communicate fluidly with a valve seat 136a to 136d, respectively. An additional valve seat 136e is placed at the intersection of flow paths 126b, 126c and patient line 56 for reasons discussed below. Heated fresh container 122 communicates fluidly with supply line 26 and flow paths 126a and 126b. Temporary spent container 124 communicates fluidly with drain line 58 and flow paths 126c and 126d. Both containers 122 and 124 communicate fluidly with patient line 56, necessitating fifth valve 136e.

Figure 6:
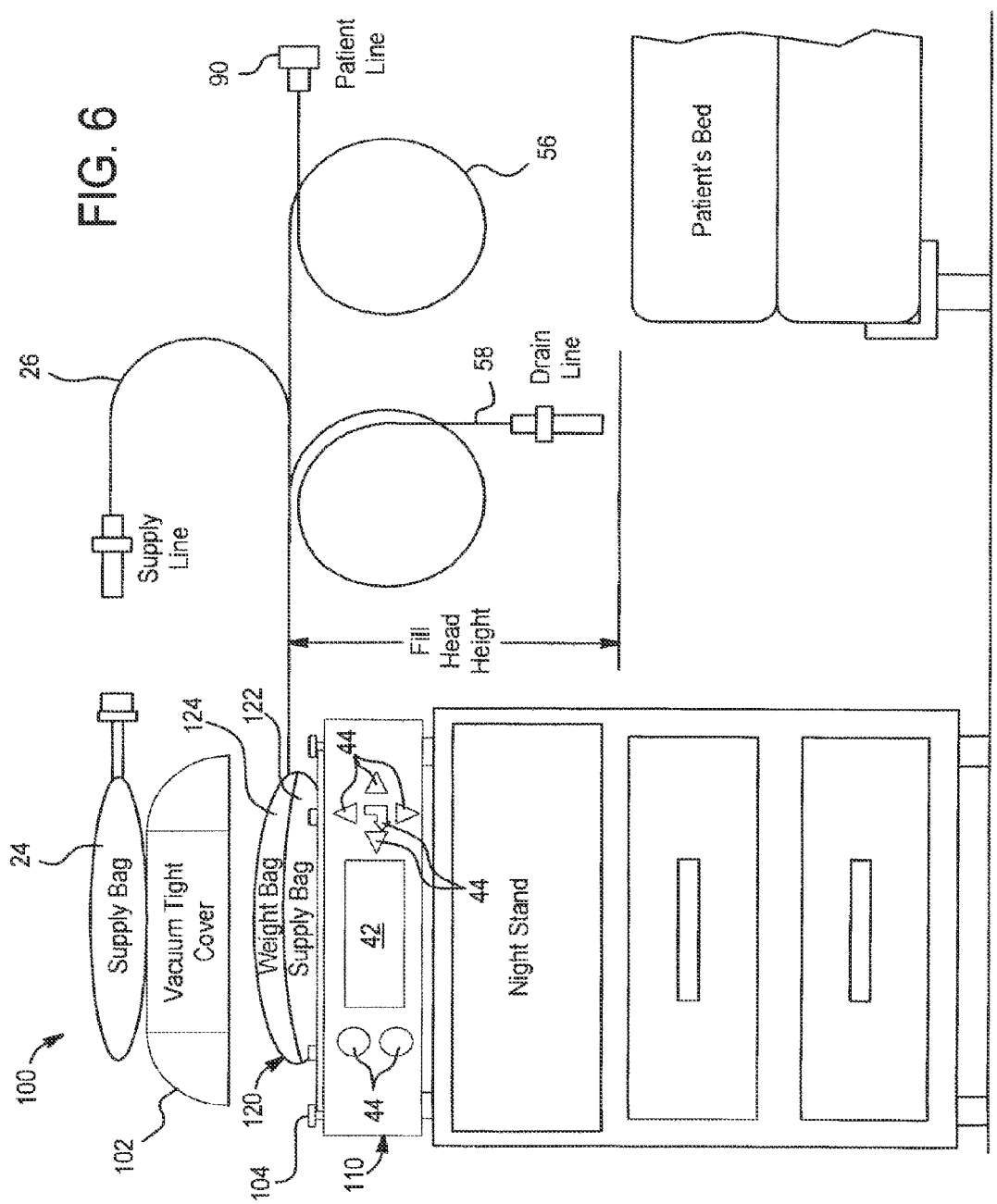
FIG. 6 is an elevation view of a second primary embodiment of an automated peritoneal dialysis system driven by gravity and vacuum.
Figure 7A:
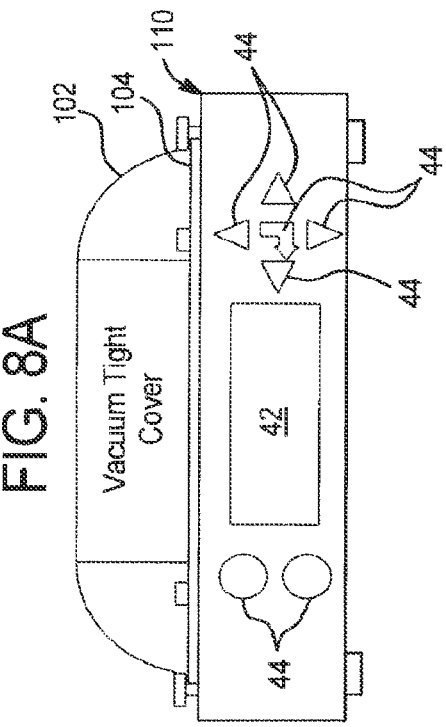
FIGS. 7A and 7B are front elevation and top plan views, respectively, of one embodiment of a control unit with an integrated heater and load cell for the system of FIG. 6, wherein a vacuum-tight cover of the system is removed.
Figure 7B:
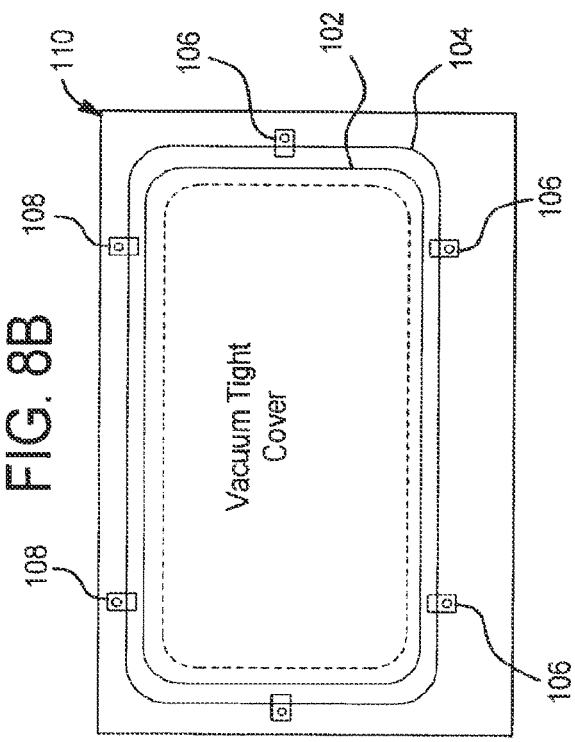
Figure 8A:
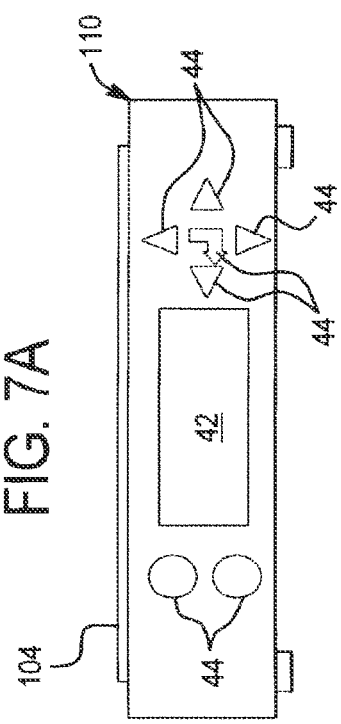
FIGS. 8A and 8B are front elevation and top plan views, respectively, of the apparatus of FIGS. 7A and 7B shown with the vacuum-tight cover in place.
Figure 8B:
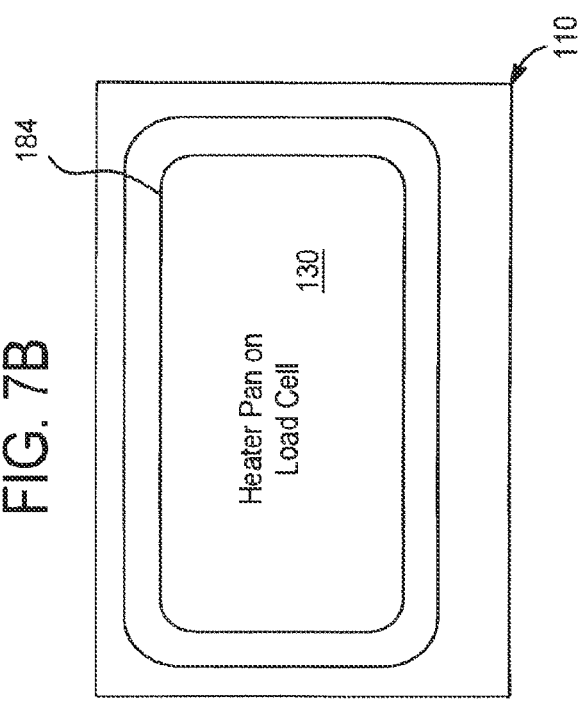

As seen in FIG. 6, control unit 110 is placed on a nightstand or other location that is elevationally above the patient's peritoneum. Dual chamber bag 120 resides above control unit 110, and therefore resides above the patient's peritoneum. Further, supply bag 24 is placed elevationally above dual chamber bag 120 and can gravity fill dual chamber bag 120. Dual chamber bag 120 in turn can gravity fill the patient's peritoneum. Furthermore, as discussed before, spent dialysate stored temporarily in spent container 124 of dual chamber bag 120 can be gravity filled into the drain container or drain bag located for example on the floor of the bedroom or other room in which therapy is taking place.

Figure 11:
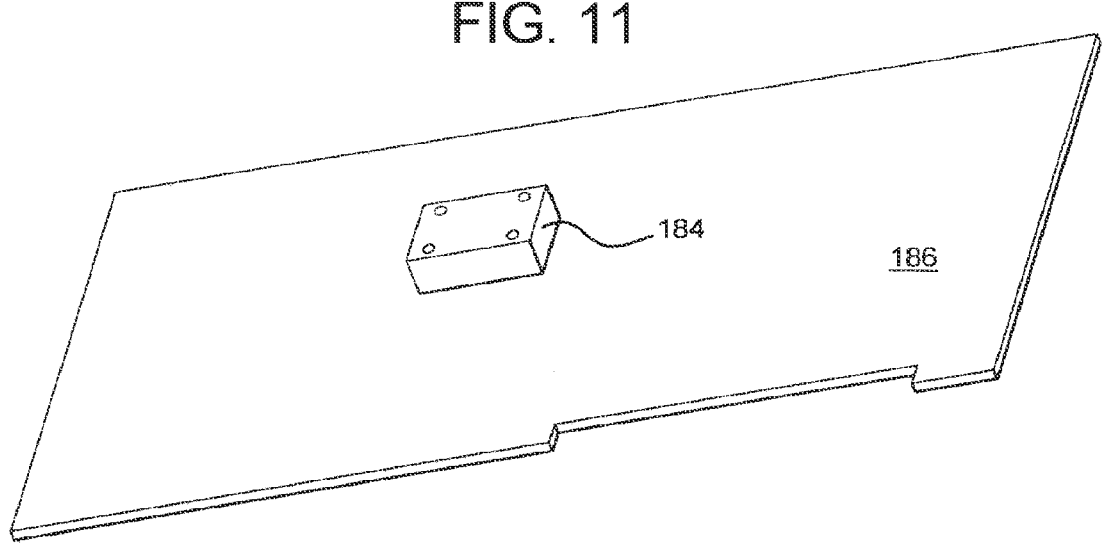
FIGS. 11 to 14 illustrate one machine configuration for the second primary embodiment of the system of FIG. 6.
Figure 12:
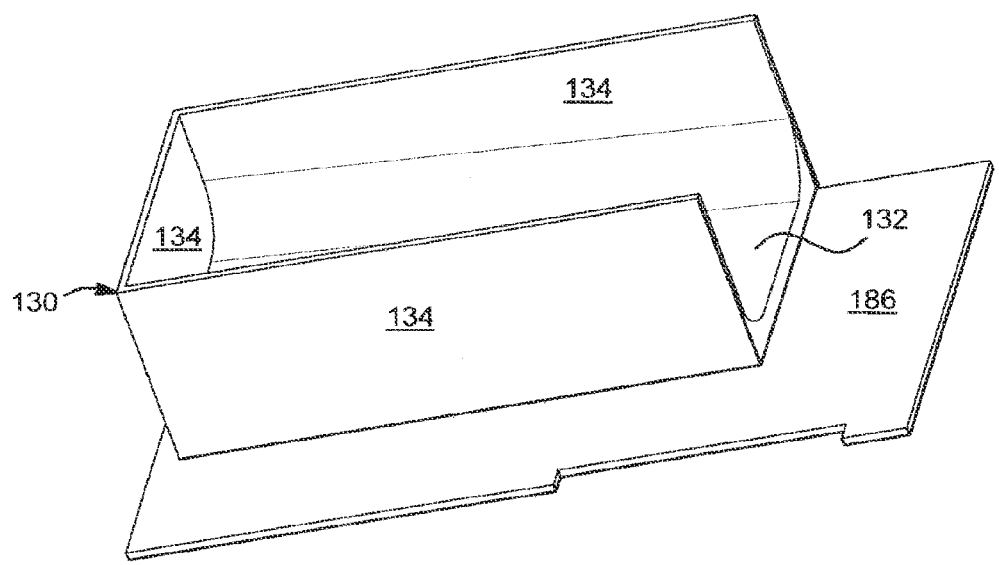

FIGS. 11 to 19 illustrate one configuration and set-up sequence for system 100. FIG. 11 illustrates that load cell 184 is mounted to a base plate 186. In one embodiment, load cell 184 is a dual load cell, which provides redundancy. Plate 186 can be hard plastic or metal, e.g., stainless steel, steel or aluminum. FIG. 12 illustrates that a heated bag holder 130 is mounted to load cell 184. Heated bag holder 130 includes heating elements (not illustrated) that heat a tapered bottom 132 and sides 134 forming the holder. Tapered bottom 132 tips the bags downwardly towards the open (line connection) end of heated bag holder 130, which helps to direct fluid out of bags 122 and 124. The transition from bottom 132 to sides 134 is chamfered or rounded to help support bags 122 and 124 and increase heater contact area.

Figure 13:
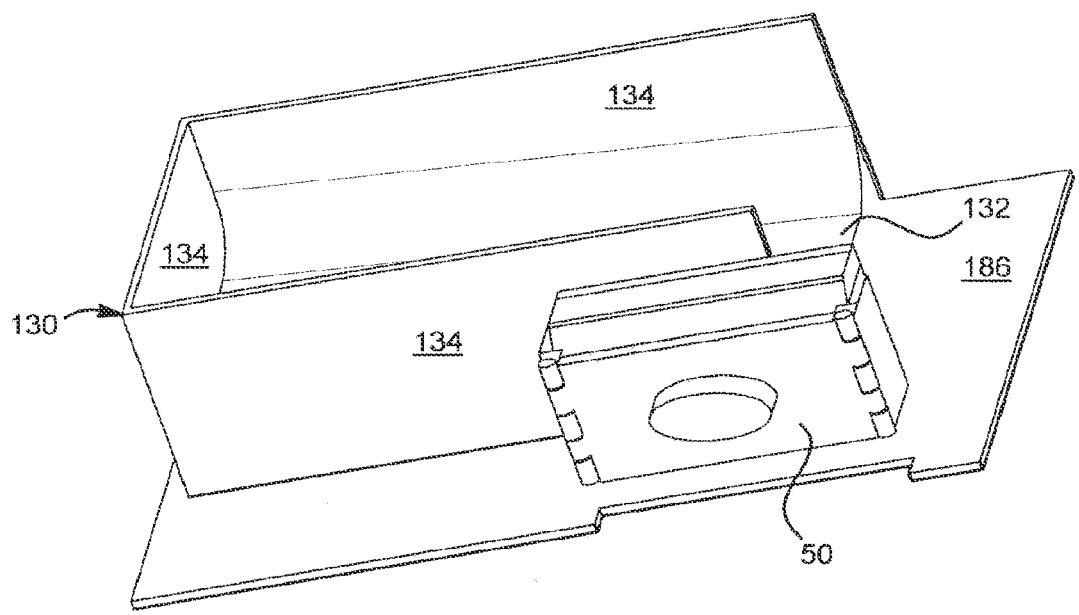
Figure 14:
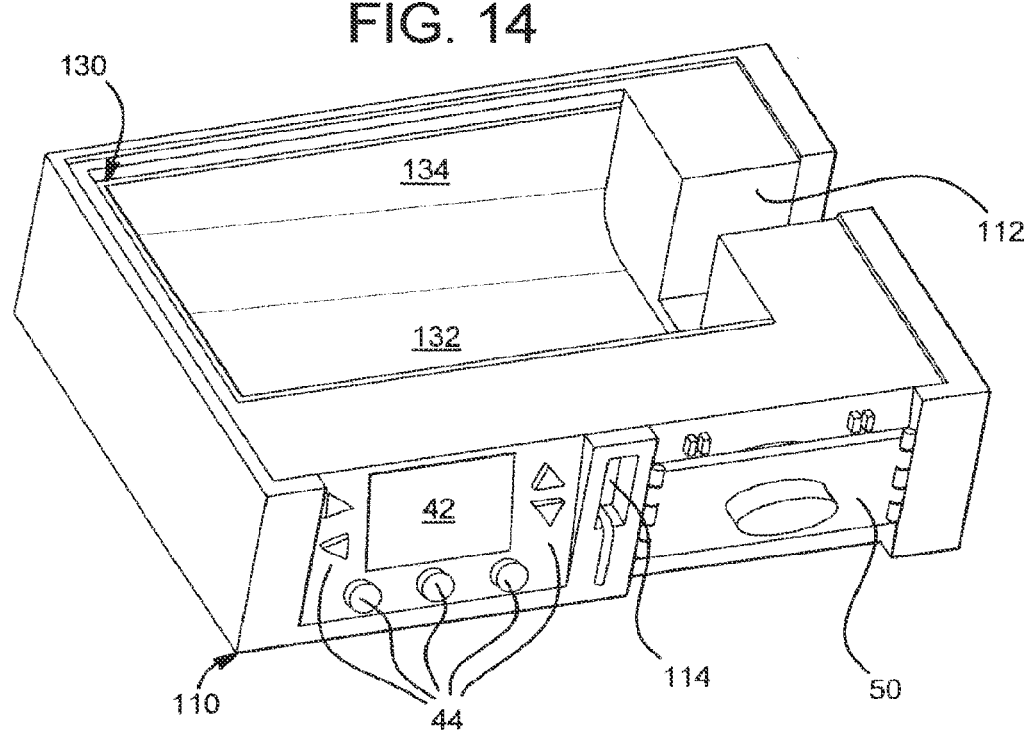

FIG. 13 illustrates that multi-way valve assembly 50 is also mounted to base plate 186. Multi-way valve assembly 50 can be the six pinch valve unit shown and described in connection with FIG. 4. FIG. 14 shows plate 186, heated bag holder 130 and multi-way valve assembly 50 mounted into control unit 110. Control unit 110 includes video monitor 42 and input devices 44 as described herein. Control unit 110 also includes or defines a slot 112 for connecting patient line 56 and drain line 58 to heating bag 122 and drain bag 124, respectively. Control unit 110 also includes or defines a line holder 114, e.g., a press-fit line holder, for fixing distal end 90 of patient line 56 for priming.

Figure 15:
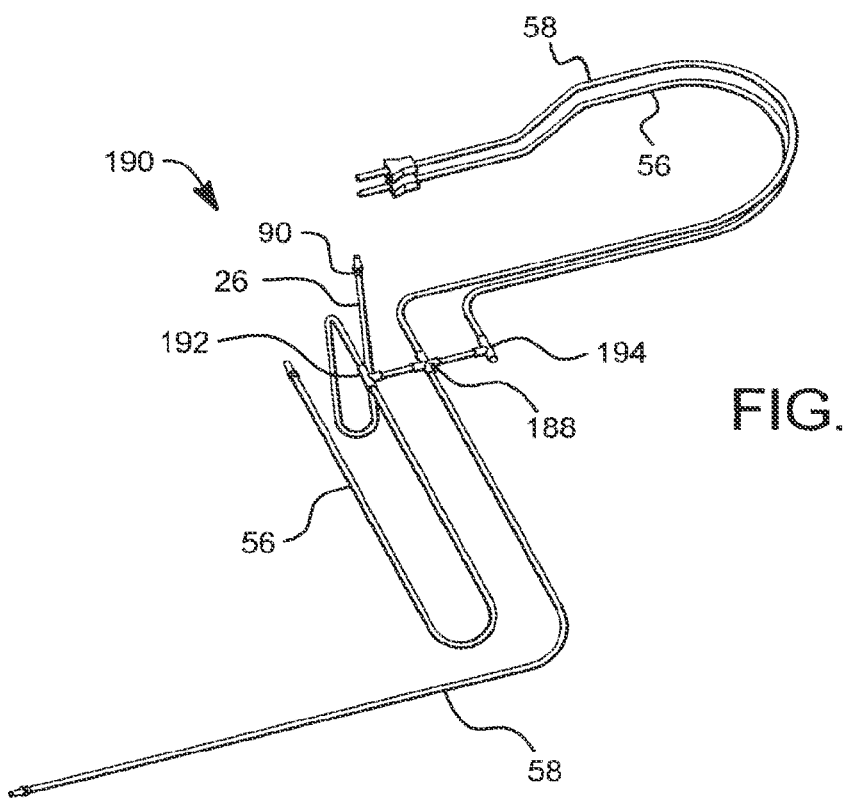
FIG. 15 illustrates a disposable set that can be used with the second primary embodiment.

FIG. 15 shows one configuration for a disposable set 190 of system 100. Disposable set 190 includes patient line 56 and drain line 58, which are connected fluidly to a cross 188. Supply line 26 tees into patient line 56 at tee 192. Patient line 56 is connected to cross 188 via elbow 194, which orients the lines properly for the loading of the area of cross 188 of disposable set 190 into control unit 110. The distal ends of lines 26, 56 and 58 are provided with connectors and clamps as needed.

Figure 16:
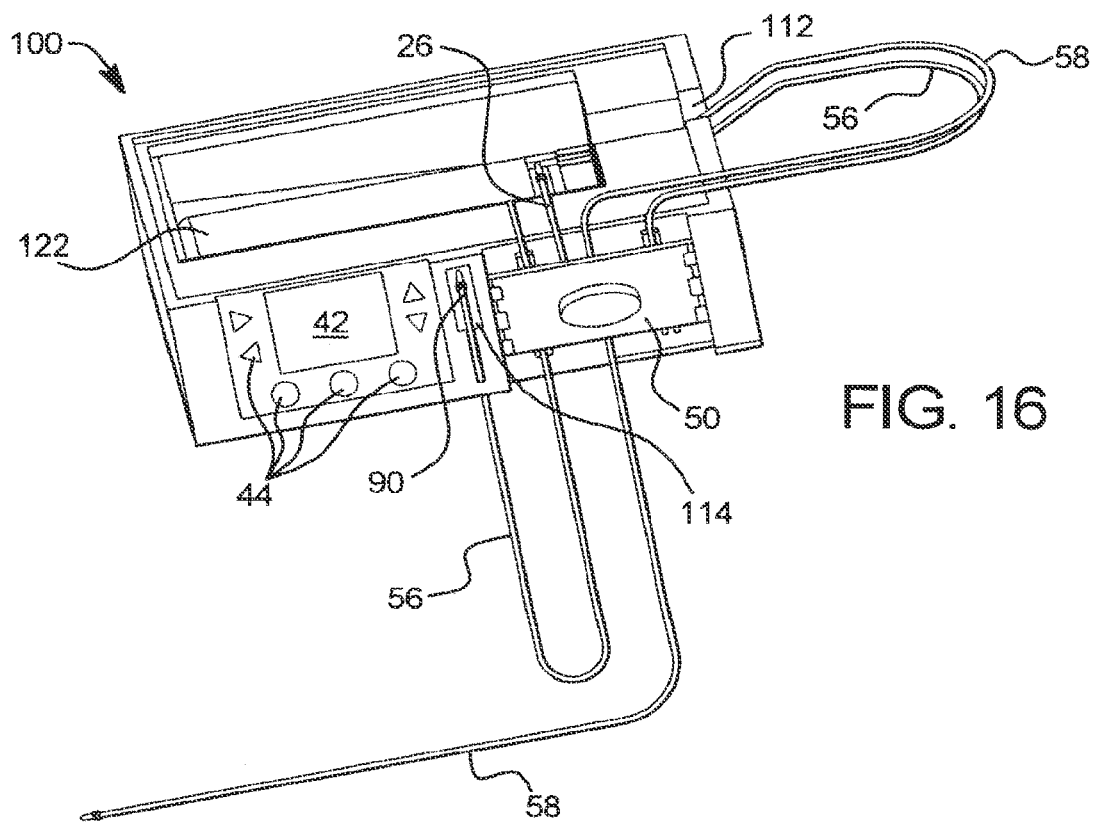
FIGS. 16 through 19 illustrate various stages in the setup sequence for an alternative arrangement for the second primary embodiment.

FIGS. 16 to 19 show a slightly different configuration for the second primary embodiment of system 100. Here, a separate heating bag 122 and supply bag 124 are used instead of dual chamber bag 120 having separate containers 122 and 124. FIG. 16 shows that the area of cross 188 of disposable set 190 has been loaded into control unit 110, and in particular behind the hinged door of multi-way valve assembly 50. The lines are placed in operable position with selected pinch valves of multi-way valve assembly 50 so that they can be opened and closed selectively. Distal end 90 of patient line 56 is fitted into line holder 114 for priming. Heating bag 122 is placed in and supported by heated bag holder 130. Patient line 56 is connected to the heating bag.

Figure 17:
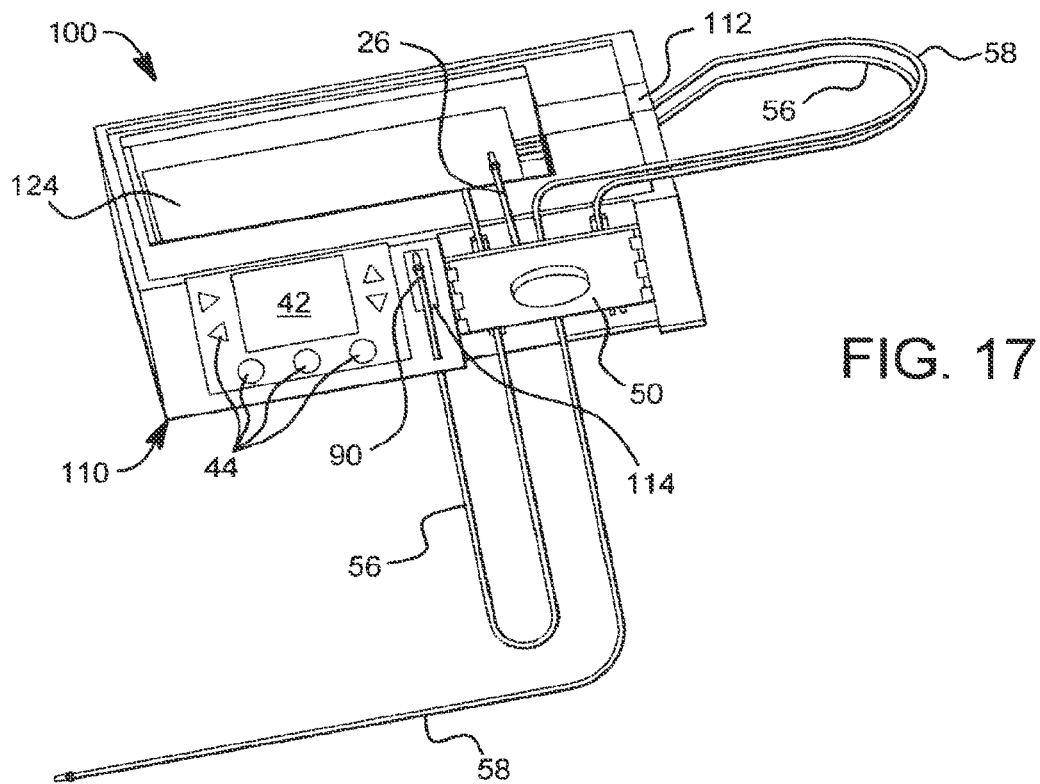
Figure 18:
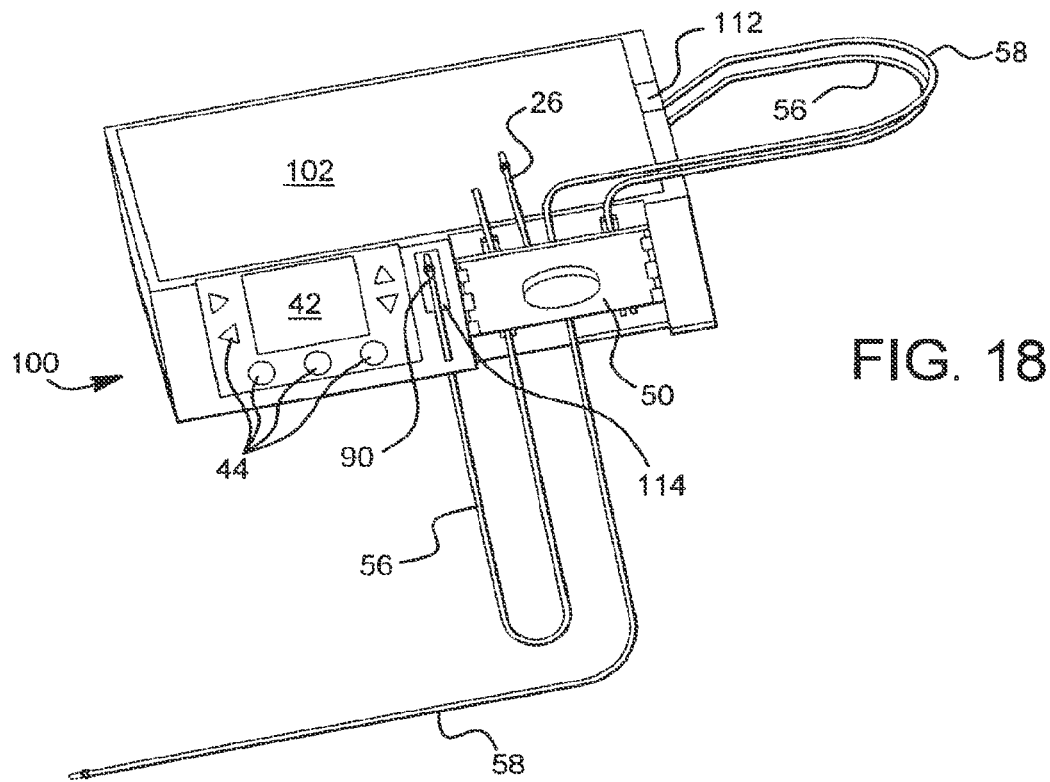
Figure 19:
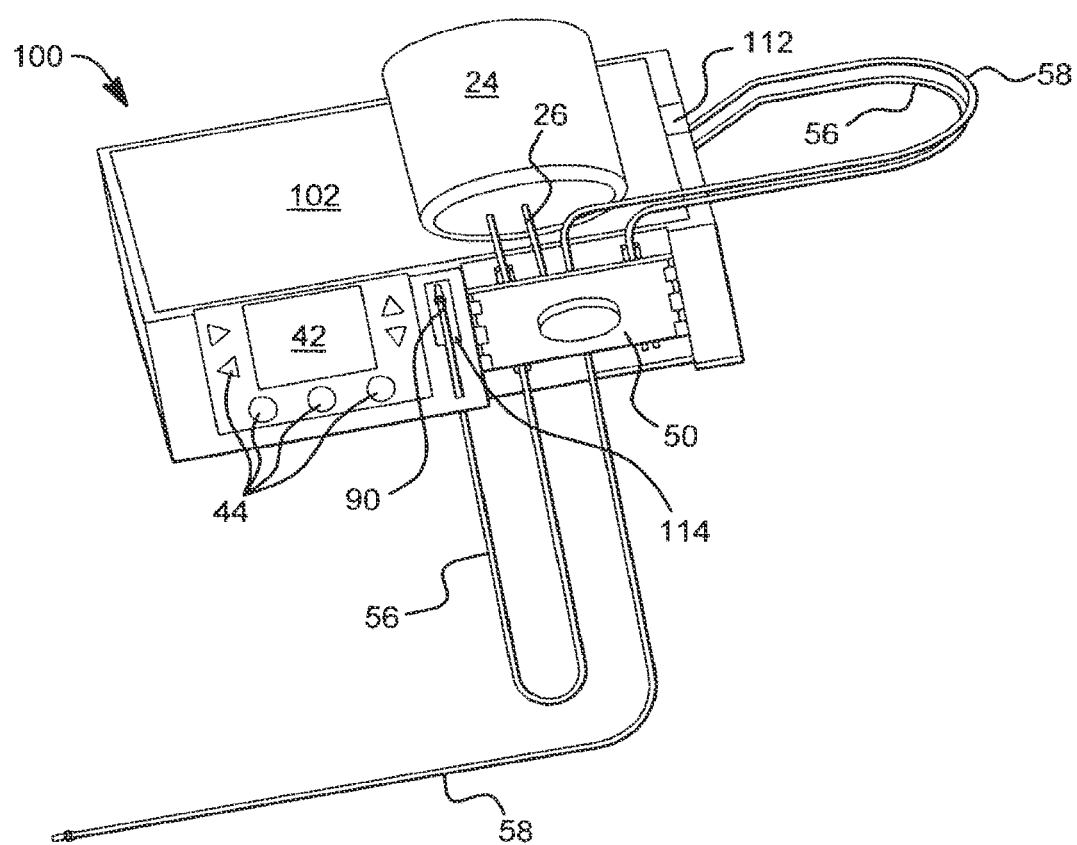

In FIG. 17, empty, interim drain bag 124 is placed onto heating bag 122. Drain line 58 is connected to the drain bag. As discussed above, in this configuration heating bag 122 and drain bag 124 are separate bags as opposed to being part of a single dual chamber bag 120. Either configuration can be used. Here, the previous day's supply bag can be used as the current day's empty interim weigh bag to reduce cost and the volume of disposable waste. In FIG. 18, cover 102 is placed over bags 122 and 124. In FIG. 19, supply bag 24 is placed onto cover 102. Supply line 26 is connected to supply bag 24. System 100 is now ready to be primed.

Whether or not dual chamber bag 120 is used or separate bags 122 and 124 are used, in the priming cycle of system 100, valve seats 136a to 136e are each opened allowing the fluid to flow throughout each of the lines. The priming purges all of the lines of air including the patient line 56. The absence of air in the lines allows load cell 184 to accurately measure the volume of fluid delivered to the patient and drained from the patient and also prevents the delivery of air to the patient. The prime does not have to fully fill heater bag 122 or dual chamber bag 120 because gravity will prevent air from being delivered from heated fresh container or bag 122 to the patient. Heated fresh container or bag 122 may be provided with a vent (not illustrated), for example including a hydrophobic membrane, which allows air to be purged from container 122 as it is filled with fluid.

The controller or PCB within control unit 110 causes the vacuum source to open the valves at valve seats 136a and 136e, which enables fresh fluid to flow from supply bag 24, through supply line 26, through flow path 126a, into and filling lower supply container 122 of dual chamber bag 120 (or separate bag 122), which contacts heater 130, through flow path 126b, through patient line 56 to distal end 90. As above with system 10, system 100 includes an apparatus that holds distal end 90 of patient line 56 at least substantially at the same elevational height as supply bag 24 during the prime cycle period. When prime is complete the patient connects distal end 90 of patient line 56 to the port stitched into the patient, which port communicates via an inserted catheter with the patient's peritoneum. During prime, the heating of fresh dialysate within supply container or bag 122 can begin.

As with system 10, the next step in the therapy in one embodiment is to remove the last-bag volume from the patient's last treatment. Before this is done, however, the weight of fresh fluid that has entered fresh container or bag 122 is noted. Afterwards, the vacuum source is allowed to: (i) open the valves at valve seats 136c and 136e and (ii) draw a vacuum within vacuum type cover 102 (valves at valve seats 126a and 126b opened previously for prime are now closed). This action causes spent fluid to be pulled from the patient's peritoneum, through line 56, and into temporary spent container 124 of dual chamber bag 120. Thus at the same time a batch of fresh dialysate from the prime is being heated, the previous last-bag volume can be pulled from the patient. The additional weight of spent fluid entering dual chamber bag 120 is noted.

As soon as the volume of fluid in supply container 122 is heated to its desired temperature, it can be delivered to the patient (assuming this does not occur before the last-bag volume is removed completely from the patient). Assuming that the heating takes longer than the last-bag removal, the temporary spent container 124 can be drained to the drain bag while the fresh fluid in the fresh container 122 is being heated. Here, control unit 110 causes the valve operating with valve seat 136d to open path 126d, enabling spent fluid to gravity drain from the temporary spent container 124 to the drain bag. If this portion of the drain occurs before the fill occurs, the drop in weight within dual chamber bag 120 can be noted via the load cell 184, so that a double-checking of the amount of fluid delivered to and from each container 122 and 124 can be made.

Once the fresh fluid in container 122 is heated to its desired temperature, the heated fresh dialysate is delivered through flow path 126b, past valve seats 136b and 136e, through patient line 56 and into the patient's peritoneum. Gas egressing from the dialysate as its being heated collects at the top of fresh container 122. The interface between flow path 126b and fresh container 122 is therefore located at or near the bottom of fresh container 122, such that only liquid flows from container 122 through patient line 56. After the known amount of fresh fluid is delivered to the patient, a dwell cycle occurs in which the fresh fluid is allowed to dwell within the patient's peritoneum, while diffusive and osmotic forces remove waste and excess water from the patient. The dwell period can last for one to two hours for example depending upon the dialysis therapy prescription.

Depending on the state of dual chamber bag 120 or separate bags during the dwell period, different fill, drain and valving sequences can occur. For example, if not already done, the controller of system 100 during the dwell cycle can cause the last-bag spent dialysate residing in temporary spent container or bag 124 to be gravity fed into the drain container. This second half fill can occur while a second fill of fresh dialysate into container 122 or bag occurs for heating. The drain of the interim spent container or bag 124 can occur simultaneously with the replenishing of the fresh container or bag 122 or sequentially since these weights are not required for the calculation. Once the first fill is removed from the patient and the second fill is heated to its desired fluid temperature, the second fill can be delivered to the patient for a second dwell period and so on.

More than likely, the initial last-bag volume has been sent to the final spent container before the first dwell occurs, so a second batch of fresh dialysate can be delivered from supply bag 24 to fresh container or bag 122 of dual chamber bag 120 for heating. Because temporary spent container or bag 124 is empty when this happens, system 100 knows the weight of the second fill fluid is equal to the weight in container or bag 122 at the end of the second fill. When the first dwell period is over, spent fluid is vacuum driven to temporary spent container or bag 124, while fluid is being heated within fresh container or bag 122. Once the first fill is removed from the patient and the second fill is heated to its desired fluid temperature, the second fill can be delivered to the patient for a second dwell period and so on. System 100 can deliver a last-bag volume at the end of treatment, which operates as described above.

Both systems 10 and 110 can perform a tidal flow peritoneal dialysis treatment as an alternative to the batch type therapies just described. In tidal flow systems, only a portion of the spent fluid is removed from the patient's peritoneum. The removed spent portion is back filled with fresh fluid. The partial exchanges occur more frequently than is done typically with batch type therapies. Tidal flow therapies are accordingly more continuous.

It should be understood that various changes and modifications to the presently preferred embodiments described herein will be apparent to those skilled in the art. Such changes and modifications can be made without departing from the spirit and scope of the present invention and without diminishing its intended advantages. It is therefore intended that such changes and modifications be covered by the appended claims.

The invention is claimed as follows:

1. A method of performing peritoneal dialysis comprising:
    locating a supply of fresh dialysis fluid above a patient's peritoneal cavity;
    fluidly communicating a supply line with the supply of fresh dialysis fluid and the patient's peritoneal cavity;
    fluidly communicating a drain line with the patient's peritoneal cavity and a drain container;
    pneumatically opening a supply line valve during a fill cycle;
    gravity filling the patient's peritoneal cavity with the supply line valve open during the fill cycle;
    pneumatically opening a drain line valve during a drain cycle; and
    draining the patient's peritoneal cavity by applying a pneumatic force to an outer surface of the drain container with the drain line valve open during the drain cycle,
    wherein a same vacuum source is used to (i) pneumatically open the supply line valve, (ii) pneumatically open the drain line valve, and (iii) apply the pneumatic force to the outer surface of the drain container.

2. The method of claim 1, which includes closing the supply and drain line valves during a dwell cycle.

3. The method of claim 2, which includes biasing the supply and drain line valves closed, and wherein closing the supply and drain line valves during the dwell cycle includes ceasing to apply a pneumatic force to the supply and drain line valves.

4. The method of claim 1, which includes locating the drain container within a vacuum-tight space, wherein draining the patient's peritoneal cavity includes applying pneumatic force to the vacuum-tight space.

5. The method of claim 1, which includes weighing at least one of the supply of fresh dialysis fluid or a volume of spent dialysis fluid drained from the patient's peritoneal cavity.

6. The method of claim 1, which includes comparing a weight of the supply of dialysis fluid to a weight of a volume of spent dialysis fluid drained from the patient's peritoneal cavity.

7. A method of performing peritoneal dialysis comprising:
setting a first flow rate for pulling spent dialysis fluid from a patient's peritoneal cavity;
pneumatically opening a drain line valve connecting the patient's peritoneal cavity to a drain container;
pulling a vacuum on the drain container at a first pressure to pull the spent dialysis fluid from the patient's peritoneal cavity at the first flow rate;
weighing the drain container;
setting a second flow rate for pulling the spent dialysis fluid from the patient's peritoneal cavity when the weight of the drain container reaches a threshold;
modifying the vacuum on the drain container to achieve the second flow rate when the weight of the drain container reaches the threshold by pulling the vacuum on the drain container at a second pressure different from the first pressure;
closing the drain line valve; and
pneumatically opening a supply line valve to allow fresh dialysis fluid to flow into the patient's peritoneal cavity.

8. The method of claim 7, which includes using a same vacuum source to: (i) pneumatically open the drain line valve; (ii) pull the vacuum on the drain container; and (iii) pneumatically open the supply line valve.

9. The method of claim 7, which includes applying a pneumatic force to a supply of fresh dialysis fluid to push the fresh dialysis fluid into the patient's peritoneal cavity.

10. The method of claim 7, which includes comparing a weight of the fresh dialysis fluid to a weight of the spent dialysis fluid.

11. The method of claim 7, which includes calculating a flowrate based on at least one of a change in a weight of the fresh dialysis fluid or a change in a weight of the spent dialysis fluid.

12. The method of claim 7, which includes gravity feeding the fresh dialysis fluid into the patient's peritoneal cavity.

13. The method of claim 7, which includes lessening the first flow rate by modifying the vacuum on the drain container to achieve the second flow rate.

14. The method of claim 7, which includes closing the supply line valve to allow the fresh dialysis fluid to dwell in the patient's peritoneal cavity.

15. The method of claim 7, wherein closing the drain line valve includes ceasing to apply a pneumatic force to the drain line valve.

16. A method of performing peritoneal dialysis comprising:
heating a supply of fresh dialysis fluid;
gravity feeding a volume of the supply of fresh dialysis fluid into a patient's peritoneal cavity;
pneumatically opening or closing at least one first valve to control the volume of fresh dialysis fluid fed into the patient's peritoneal cavity;
draining a volume of spent dialysis fluid from the patient's peritoneal cavity by applying a pneumatic force to an outer surface of a drain container; and
pneumatically opening or mechanically closing at least one second valve to control the volume of spent dialysis fluid drained from the patient's peritoneal cavity,
wherein a same vacuum source is used to (i) pneumatically open the at least one first valve, (ii) apply the pneumatic force to the outer surface of the drain container, and (iii) pneumatically open the at least one second valve.

17. The method of claim 16, which includes locating the drain container within a vacuum-tight space.

18. The method of claim 17, wherein draining the volume of spent dialysis fluid from the patient's peritoneal cavity includes applying the pneumatic force to the vacuum-tight space.

19. The method of claim 16, which includes weighing at least one of: (i) the volume of fresh dialysis fluid fed into the patient's peritoneal cavity, or (ii) the volume of spent dialysis fluid drained from the patient's peritoneal cavity.

20. A method of performing peritoneal dialysis comprising:
setting a first flow rate for pulling spent dialysis fluid from a patient's peritoneal cavity;
applying a vacuum at a first pressure to pull a volume of the spent dialysis fluid from the patient's peritoneal cavity at the first flow rate ;
weighing the volume of spent dialysis fluid;
setting a second flow rate for pulling the spent dialysis fluid from the patient's peritoneal cavity when the weight of the volume of spent dialysis fluid reaches a threshold;
adjusting the flow of spent dialysis fluid from the patient's peritoneal cavity to achieve the second flow rate when the weight of the volume of spent dialysis fluid reaches the threshold by applying the vacuum at a second pressure different from the first pressure;
calculating a volume of fresh dialysis fluid to supply to the patient's peritoneal cavity based on the weight of the volume of spent dialysis fluid; and
applying the vacuum to at least one valve to allow the volume of fresh dialysis fluid to flow into the patient's peritoneal cavity.

21. A method of performing peritoneal dialysis comprising:
pneumatically opening a drain line valve connecting a patient's peritoneal cavity to a drain container;
pulling a vacuum on the drain container to pull spent dialysis fluid from the patient's peritoneal cavity;
weighing the drain container;
modifying the vacuum on the drain container based on the weight of the drain container;
closing the drain line valve; and
pneumatically opening a supply line valve to allow fresh dialysis fluid to flow into the patient's peritoneal cavity,
wherein a same vacuum source is used to: (i) pneumatically open the drain line valve; (ii) pull the vacuum on the drain container; and (iii) pneumatically open the supply line valve.

* * * * *

UNITED STATES PATENT AND TRADEMARK OFFICE
CERTIFICATE OF CORRECTION

PATENT NO. : 9,585,993 B2
APPLICATION NO. : 14/079321
DATED : March 7, 2017
INVENTOR(S) : Childers et al.

It is certified that error appears in the above-identified patent and that said Letters Patent is hereby corrected as shown below:

In the Claims

In Column 18, Line 65, insert the word --and-- before the word "wherein".

In Column 18, Line 66, insert the word --the-- before the word "pneumatic".

In Column 19, Line 59, insert the word --mechanically-- before the word "closing".

Signed and Sealed this
Thirteenth Day of June, 2017

Joseph Matal
*Performing the Functions and Duties of the
Under Secretary of Commerce for Intellectual Property and
Director of the United States Patent and Trademark Office*